(12) United States Patent
Gerber et al.

(10) Patent No.: US 10,124,274 B2
(45) Date of Patent: Nov. 13, 2018

(54) REPLENISHING UREASE IN DIALYSIS SYSTEMS USING UREASE POUCHES

(71) Applicant: Medtronic, Inc., Minneapolis, MN (US)

(72) Inventors: Martin T. Gerber, Maple Grove, MN (US); Christopher M. Hobot, Tonka Bay, MN (US)

(73) Assignee: Medtronic, Inc., Minneapolis, MN (US)

( * ) Notice: Subject to any disclaimer, the term of this patent is extended or adjusted under 35 U.S.C. 154(b) by 348 days.

(21) Appl. No.: 14/644,576

(22) Filed: Mar. 11, 2015

(65) Prior Publication Data

US 2015/0367060 A1 Dec. 24, 2015

Related U.S. Application Data

(60) Provisional application No. 62/016,613, filed on Jun. 24, 2014, provisional application No. 62/077,169, filed on Nov. 7, 2014.

(51) Int. Cl.
*B01D 15/20* (2006.01)
*A61M 1/16* (2006.01)

(52) U.S. Cl.
CPC ......... *B01D 15/203* (2013.01); *A61M 1/1696* (2013.01); *A61M 2202/0057* (2013.01); *A61M 2205/18* (2013.01); *A61M 2205/33* (2013.01)

(58) Field of Classification Search
CPC ........ A61M 1/1696; A61M 2202/0057; A61M 2202/0498; A61M 2205/12; A61M 2205/18; A61M 2205/33; A61M 2205/3337; B01D 15/08; B01D 15/203; B01D 61/243

See application file for complete search history.

(56) References Cited

U.S. PATENT DOCUMENTS

| | | |
|---|---|---|
| 3,608,729 A | 9/1971 | Haselden |
| 3,669,880 A | 6/1972 | Marantz |
| 3,776,819 A | 12/1973 | Williams |
| 3,850,835 A | 11/1974 | Marantz |
| 3,884,808 A | 5/1975 | Scott |

(Continued)

FOREIGN PATENT DOCUMENTS

| | | |
|---|---|---|
| CN | 104936633 | 9/2015 |
| EP | 711182 B1 | 6/2003 |

(Continued)

OTHER PUBLICATIONS

PCT/US2014/065950 International Search Report and Written Opinion dated Feb. 24, 2015.

(Continued)

*Primary Examiner* — John Kim
(74) *Attorney, Agent, or Firm* — Kenneth Collier; Roger Hahn

(57) ABSTRACT

An apparatus and method for replenishing urease in a sorbent cartridge for use in sorbent dialysis using urease pouches. The sorbent cartridge is configured to allow insertion of a urease pouch or injection of a urease solution into the sorbent cartridge containing a urease pouch. The sorbent module can also comprise other, rechargeable, sorbent materials for removing toxins other than urea from spent dialysate.

16 Claims, 16 Drawing Sheets

(56) References Cited

U.S. PATENT DOCUMENTS

| | | |
|---|---|---|
| 3,902,490 A | 9/1975 | Jacobsen et al. |
| 3,989,622 A * | 11/1976 | Marantz .............. A61M 1/1696 210/645 |
| 4,094,775 A | 6/1978 | Mueller |
| 4,206,054 A | 6/1980 | Moore |
| 4,209,392 A | 6/1980 | Wallace |
| 4,376,707 A | 3/1983 | Lehmann |
| 4,460,555 A | 7/1984 | Thompson |
| 4,581,141 A | 4/1986 | Ash |
| 4,650,587 A | 3/1987 | Polak |
| 4,684,460 A | 8/1987 | Issautier |
| 5,230,702 A | 7/1993 | Lindsay et al. |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Indriksons |
| 5,849,179 A | 12/1998 | Emerson et al. |
| 5,858,186 A | 1/1999 | Glass |
| 5,944,684 A | 8/1999 | Roberts |
| 6,036,858 A | 3/2000 | Carlsson |
| 6,114,176 A | 9/2000 | Edgson et al. |
| 6,126,831 A | 10/2000 | Goldau et al. |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,283 B2 | 4/2005 | Thompson |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor |
| 7,276,042 B2 | 10/2007 | Polaschegg |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,566,432 B2 | 7/2009 | Wong |
| 7,597,806 B2 | 10/2009 | Uchi |
| 7,776,210 B2 | 8/2010 | Rosenbaum |
| 7,794,419 B2 | 9/2010 | Paolini et al. |
| 7,850,635 B2 | 12/2010 | Polaschegg |
| 7,922,686 B2 | 4/2011 | Childers et al. |
| 7,922,911 B2 | 4/2011 | Micheli |
| 7,947,179 B2 | 5/2011 | Rosenbaum |
| 7,955,290 B2 | 6/2011 | Karoor et al. |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 11/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,187,250 B2 | 5/2012 | Roberts |
| 8,197,439 B2 | 6/2012 | Wang et al. |
| 8,303,532 B2 | 11/2012 | Hamada et al. |
| 8,404,491 B2 | 3/2013 | Li et al. |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 9,144,640 B2 | 9/2015 | Pudil |
| 2001/0007931 A1 | 7/2001 | Blatter |
| 2002/0112609 A1 * | 8/2002 | Wong .................. A61M 1/1696 96/131 |
| 2002/0117436 A1 | 8/2002 | Rajan |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2004/0019312 A1 | 1/2004 | Childers et al. |
| 2004/0099593 A1 | 5/2004 | DePaolis |
| 2004/0147900 A1 | 7/2004 | Polaschegg |
| 2004/0257409 A1 | 12/2004 | Cheok |
| 2005/0006296 A1 | 1/2005 | Sullivan |
| 2005/0113796 A1 | 5/2005 | Taylor |
| 2005/0150832 A1 | 7/2005 | Tsukamoto |
| 2005/0274658 A1 | 12/2005 | Rosenbaum |
| 2006/0037483 A1 * | 2/2006 | Kief, Jr. .............. A47J 31/4467 99/295 |
| 2006/0241543 A1 | 10/2006 | Gura |
| 2007/0007208 A1 | 1/2007 | Brugger et al. |
| 2007/0179431 A1 | 8/2007 | Roberts |
| 2007/0213665 A1 | 9/2007 | Curtin |
| 2008/0006570 A1 | 1/2008 | Gura |
| 2008/0051696 A1 | 2/2008 | Curtin |
| 2008/0053905 A9 | 3/2008 | Brugger et al. |
| 2008/0217245 A1 | 9/2008 | Rambod |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0157877 A1 | 6/2009 | Baek |
| 2009/0216045 A1 | 8/2009 | Singh |
| 2010/0004588 A1 | 1/2010 | Yeh |
| 2010/0007838 A1 | 1/2010 | Fujimoto |
| 2010/0078381 A1 | 4/2010 | Merchant |
| 2010/0084330 A1 | 4/2010 | Wong |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114012 A1 | 5/2010 | Sandford |
| 2010/0217181 A1 | 8/2010 | Roberts |
| 2010/0224492 A1 | 9/2010 | Ding et al. |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding et al. |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0248017 A1 | 10/2012 | Beiriger |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0190885 A1 | 7/2014 | Meyer |
| 2014/0217028 A1 | 8/2014 | Pudil |
| 2014/0251908 A1 | 9/2014 | Ding |
| 2014/0276374 A1 * | 9/2014 | Minkus ................ A61M 1/288 604/28 |
| 2014/0326671 A1 | 11/2014 | Kelly |
| 2015/0057602 A1 | 2/2015 | Mason |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258266 A1 | 9/2015 | Merchant |
| 2015/0306292 A1 | 10/2015 | Pudil |

(56) References Cited

U.S. PATENT DOCUMENTS

| | | |
|---|---|---|
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |

FOREIGN PATENT DOCUMENTS

| | | |
|---|---|---|
| EP | 1592494 B1 | 6/2009 |
| EP | 2575827 A2 | 12/2010 |
| EP | 2576453 A2 | 12/2011 |
| EP | 1545652 B1 | 1/2013 |
| EP | 1345856 B1 | 3/2013 |
| EP | 2344220 B1 | 4/2013 |
| WO | 9532010 A1 | 11/1995 |
| WO | 0185295 A2 | 11/2001 |
| WO | 200243859 | 6/2002 |
| WO | 2002043859 | 6/2002 |
| WO | 2003043677 A2 | 5/2003 |
| WO | 2003051422 A2 | 6/2003 |
| WO | 2004064616 A2 | 8/2004 |
| WO | 2004062710 A3 | 10/2004 |
| WO | 2005123230 A2 | 12/2005 |
| WO | 2007089855 A2 | 8/2007 |
| WO | 2008075951 A1 | 6/2008 |
| WO | 2009157877 A1 | 12/2009 |
| WO | 2009157878 A1 | 12/2009 |
| WO | 2010028860 A1 | 3/2010 |
| WO | 2010102190 A4 | 11/2010 |
| WO | 2010141949 | 12/2010 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 | 2/2013 |
| WO | 2013028809 A3 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | 2015142624 | 9/2015 |
| WO | 2015199764 | 12/2015 |

OTHER PUBLICATIONS

PCT/US2015/032492 International Search Report dated Nov. 17, 2015.
PCT/US2015/016270 International Search Report and Written Opinion dated Jun. 5, 2015.
PCT/US2015/016273 International Search Report and Written Opinion dated Jun. 9, 2015.
PCT/US2015/032492 Written Opinion dated Nov. 17, 2015.
PCT/US2015/032492 International Search Report dated Nov. 19, 2015.
PCT/US2015/032492 Written Opinion dated Nov. 19, 2015.
PCT/US2015/020044 International Search Report Written Opinion dated Jun. 30, 2015.
PCT/US15/18587 International Preliminary Report on Patentability dated Jun. 6, 2016.
PCT/US2015/020046 International Search Report and Written Opinion dated Jun. 29, 2015.
International Search Report from PCT/US2012/051946, dated Feb. 28, 2013.
Office Action for Chinese Application No. 2015/80009562.5 dated Jul. 3, 2017.
International Preliminary Report on Patentability for Application No. PCT/US2015/032492 dated Jun. 30, 2017.
International Preliminary Report on Patentability for Application No. PCT/US2015/016273 dated Feb. 19, 2016.
US2015/019881 Written Opinion dated Jun. 16, 2016.
US2015/019881 Written Opinion dated May 9, 2016.
US2015/019881 International Search Report and Written Opinion dated Jun. 29, 2015.
European Search Report for App. No. 15751391.2 dated Aug. 4, 2017.
European Search Report and supplementary Search Report for App. No. 14865374.4 dated Jun. 12, 2017.
European Search Report for EP 15811439, dated Feb. 15, 2018.
European Search Report for EP App. No. 15811573.3, dated Feb. 15, 2018.
European Search Report for EP App. No. 15810804.3, dated Feb. 15, 2018.

* cited by examiner

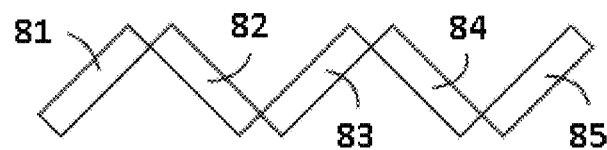
FIG. 9a
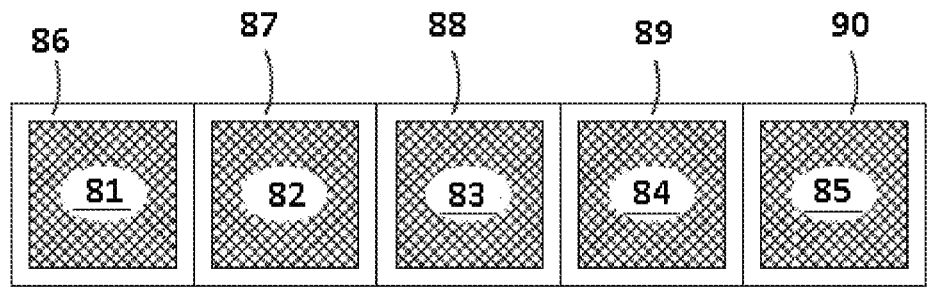
FIG. 9b
FIG. 9c

REPLENISHING UREASE IN DIALYSIS SYSTEMS USING UREASE POUCHES

FIELD OF THE INVENTION

The invention relates to compositions and related methods for replenishing urease in modules, sections, or compartments of a sorbent cartridge. The urease can be replenished by adding one or more urease pouches containing urease of varying sizes and configurations to the sorbent cartridge, or by injecting a urease solution into a sorbent cartridge containing a urease pouch. The sorbent cartridge can be divided into a first section and a second section wherein the first section of the sorbent cartridge can contain urease, which can be added by the urease pouches of the present invention as needed before, during, or after dialysis and a second section can contain other sorbent materials excluding urease such as zirconium phosphate.

BACKGROUND

Urease is a water soluble enzyme used in dialysis to convert urea into ammonium ions and bicarbonate. Oftentimes, urease can be immobilized electrostatically, covalently, or by adsorption on an alumina or silica substrate inside a sorbent cartridge that is designed to be connected to a dialysis system. However, conventional immobilization of urease has been associated with the disadvantages of low loading and leaching of urease that can result in insufficient amounts of urease for dialysis. Moreover, conventional sorbent dialysis systems cannot replenish, i.e., provide additional or specified amounts of urease, to the known sorbent cartridges or dialysis systems. The inability to add urease, and control the amount of urease added, to the sorbent system use can be problematic because the amount of urease required for a particular dialysis session can vary. The amount of urease required for a dialysis session may depend on a number of factors such as patient weight, urea load, dialysis time, etc. resulting in different rates and amounts of urease required per session. Using more or less than the required amount of urease for a particular dialysis session can translate into increased expenditures and waste from unused or overused urease as well as other sorbent materials contained in the sorbent cartridge.

Known sorbent dialysis cartridges and systems further cannot measure the amount of urease used during a particular session or even replenish or add urease back to the sorbent cartridge or system during operation as needed, should a session need additional quantities of urease or should additional urease be needed in the case of faster fluid flow rates through the sorbent cartridge. Sometimes, certain sorbent materials such as alumina and zirconium phosphate can be recharged such that the sorbent material is put back into a condition for use in sorbent based dialysis (see U.S. application Ser. No. 14/261,651). As such, known sorbent systems cannot recharge some or all of the sorbent materials, some of which can be rechargeable components within the sorbent cartridge, without undesirable effects. For example, recharging zirconium phosphate in the same sorbent cartridge in which urease is immobilized on alumina can result in urease, which is bound to an alumina layer, being stripped off the alumina. More generally, recharging certain rechargeable sorbent materials in known sorbent cartridges can sometimes have undesirable effects on other sorbent materials contained inside the same sorbent cartridge. Known systems cannot replenish such urease lost due to recharging of other sorbent materials, or add a specific amount of urease to a sorbent cartridge or sorbent system during operation.

As such, there is a need for systems, methods, components and devices for optimizing use of sorbent materials such as urease within a sorbent cartridge. The need extends to systems that can replenish urease in a sorbent cartridge, and related systems, by either directly adding discrete amounts of urease or by continuously adding urease to the sorbent system by a delivery mechanism. The need includes a sorbent cartridge and related systems in which urease can be added on demand, continuously, and in specified, discrete amounts. The need extends to providing urease at a specified time such as after, before, or during a dialysis session. The need includes providing the urease while the system is operating or off-line. There is also a need for a modular system, such as a system of different sized urease pouches that contain urease of different quantities that can be easily added to a sorbent cartridge and related systems. The need includes adding the desired amounts of urease in a simple and convenient manner and in adjustable amounts. The need includes a sorbent cartridge having a section wherein an adjustable amount of urease can be added. There is also a need for a sorbent cartridge having a section for containing adjustable amounts of urease. The need includes a sorbent cartridge optionally having a section for containing one or more sorbent materials that can be in a fixed amount. In general, the need can be broadly described as dynamically adding urease to sorbent cartridges and related dialysis systems. The need can include adjusting the amount of required urease depending on a measured amount of ammonia detected anywhere in the system or sorbent cartridge.

There is a further need for a closed sorbent cartridge capable of receiving an adjustable amount of urease, on demand. The need includes methods for measuring, refilling, and/or replenishing urease during a dialysis session. The methods and systems require a way for introducing urease in continuous or specified and/or discrete amounts. The methods and systems may involve pre-set amounts of urease or dynamically adjustable amounts of urease. There is also a need for a system capable of replenishing urease that may be stripped out of the sorbent cartridge lost during maintenance or during a dialysis session.

SUMMARY OF THE INVENTION

The first aspect of the invention relates to a sorbent cartridge. In any embodiment of the first aspect of the invention, the sorbent cartridge can comprise a first section having a urease introducer configured to receive urease via one or more urease pouch.

In any embodiment of the first aspect of the invention, the sorbent cartridge can comprise a second section configured to contain one or more sorbent materials; and a fluid connection fluidly connecting the first section to at least one additional section. The at least one additional section can be described in any embodiment of the first aspect of the invention as a second section. In any embodiment of the first aspect of the invention, the sorbent materials can be rechargeable.

In any embodiment of the first aspect of the invention, the urease introducer can be selected from any one of: a urease injection port in fluid communication with either the first section or an inlet of the sorbent cartridge; a urease tray slideably disposed on the first section; and a urease door disposed on an exterior side of the sorbent cartridge allowing access into an interior of the first section.

In any embodiment of the first aspect of the invention, the urease tray and interior of the first section can be adapted to receive either a urease pouch containing urease or solid urease.

In any embodiment of the first aspect of the invention, the urease pouch or solid urease can contain alumina, silica, or a combination thereof.

In any embodiment of the first aspect of the invention, the urease pouch can have a planar base with upwardly extending walls connecting to a planar top wherein the walls are constructed from a rigid, fluid impermeable material.

In any embodiment of the first aspect of the invention, the urease pouch can have a base and top that are circular and wherein the upwardly extending walls (a) extend parallel to the flow path, (b) slope inward to an axis of the sorbent cartridge wherein the top has a smaller surface area than the base or (c) slope upwardly outward from the axis of the disc shape wherein the top has a larger surface area than the base.

In one embodiment of the first aspect of the invention, the urease pouch can be formed from a porous material, the porous material allowing fluid to pass through the urease pouch and substantially retaining the urease in the urease pouch.

In any embodiment of the first aspect of the invention, the urease pouch can have any one of (i) a top of the urease pouch having a pore size small enough to prevent urease from passing through and a bottom portion of the urease pouch having a pore size to allow urease to pass through; (ii) a top of the urease pouch having a pore size to allow urease to pass through and a bottom portion of the urease pouch having a pore size small enough to prevent urease from passing through; or (iii) a top of the urease pouch having a pore size to allow urease to pass through and a bottom portion of the urease pouch having a pore size to allow urease to pass through.

In any embodiment of the first aspect of the invention, the urease pouch can have a shape selected from the group consisting of a circular shape, a square shape, a triangular shape, a rectangular shape, a disc shape, a cylindrical shape, a spherical shape, a substantially rectangular shape, or a cubical shape.

In any embodiment of the first aspect of the invention, the first section can further comprise at least one additional sorbent material selected from the group consisting essentially of activated carbon, zirconium oxide, alumina, silica, and combinations thereof, and the one or more sorbent materials in the second section can be selected from any of zirconium phosphate, zirconium oxide, activated carbon, alumina, silica, and combinations thereof.

In any embodiment of the first aspect of the invention, the one or more sorbent materials in either the first or second section can be rechargeable.

In any embodiment of the first aspect of the invention, the second section can be multi-use and the first section can be single use.

In any embodiment of the first aspect of the invention, the sorbent cartridge can have an inlet and an outlet for fluid connection to a controlled compliant dialysis flow path.

In any embodiment of the first aspect of the invention, the sorbent cartridge can further comprise a urea sensor disposed in a fluid flow path such that the urea sensor contacts fluid exiting the first section and can further comprise an alert that is triggered if the urea sensor detects urea in fluid exiting the first section.

In any embodiment of the first aspect of the invention, the sorbent cartridge can further comprise a valve disposed on the urease injection port for controlling an introduction of a urease solution into the first section.

In any embodiment of the first aspect of the invention, the urease introducer can be configured to receive an adjustable amount of urease or a fixed amount of urease.

Any of the features disclosed as being part of the first aspect of the invention can be included in the first aspect of the invention, either alone or in combination.

The second aspect of the invention relates to a method that can comprise the step of adding either solid urease or a urease solution to a sorbent cartridge adapted to replenish urease in the sorbent cartridge.

In any embodiment of the second aspect of the invention, the step of adding the solid urease can comprise removing a urease pouch having a reduced amount of urease, if present, and then adding a fresh urease pouch into the sorbent cartridge.

In any embodiment of the second aspect of the invention, the step of adding the urease solution can comprise injecting a urease solution into the sorbent cartridge having a concentration between any of 1 mg/mL to 250 mg/mL, 15 mg/mL to 150 mg/mL, 10 mg/mL to 100 mg/mL, or 75 mg/mL to 250 mg/mL of urease into the sorbent cartridge.

In any embodiment of the second aspect of the invention, the urease pouch or section can contain alumina, silica, or a combination thereof.

In any embodiment of the second aspect of the invention, the method can comprise recharging an amount of one or more sorbent materials contained in the sorbent cartridge by passing a solution containing an appropriate amount of solutes for recharging the one or more rechargeable sorbent materials through the sorbent cartridge.

In any embodiment of the second aspect of the invention, the method can comprise recharging an amount of one or more sorbent materials by replacing one or more modules of a modular regeneration assembly containing an amount of one or more sorbent materials.

In any embodiment of the second aspect of the invention, a urease binding material such as alumina or silica substrate in the sorbent cartridge can be "recharged" once the sorbent cartridge is replenished with urease. Thereby, a single cartridge design with all non-water soluble, rechargeable components can be provided to simplify design and reduce cost per session.

Any of the features disclosed as being part of the second aspect of the invention can be included in the second aspect of the invention, either alone or in combination.

BRIEF DESCRIPTION OF THE DRAWINGS

FIG. 9a is a side view of a string of rectangular urease pouches.

FIG. 9b is a top view of a string of rectangular urease pouches.

FIG. 9c is a top view of a string of rectangular urease pouches connected by their edges.

DETAILED DESCRIPTION OF THE INVENTION

Figure 1:
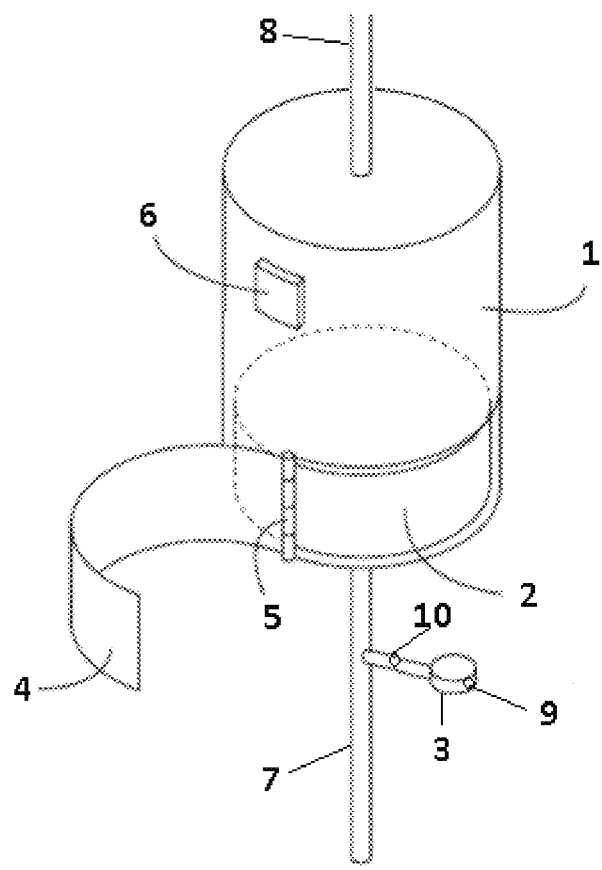
FIG. 1 shows a sorbent cartridge having a urease pouch, a urease door, and a urease injection port.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "adapted to receive" refers to a component wherein introduction of a substance into the component is possible.

An "adhesive" is any substance known in the art for use in affixing one surface to another surface, or to seal two surfaces together.

An "adjustable amount" refers to an amount of a material such as a sorbent material that can be, but is not required to be changed during a dialysis session.

An "ammonium sensor" is a sensor that is capable of detecting the presence of, or concentration of, ammonium ions.

The term "appropriate amount of solutes" refers to an amount of one or more solute(s) that is sufficient to accomplish a particular task. For example, an "appropriate amount of solutes" necessary to recharge the zirconium phosphate in a sorbent cartridge is the amount of sodium and hydrogen necessary to recharge the zirconium phosphate. The appropriate amount can be greater than the minimum amount necessary to accomplish the particular task.

An "axis of the urease pouch" describes an imaginary line running vertically through the center of the urease pouch, situated in the center of the surface of the urease pouch when viewed from the top perspective.

A "blood urea nitrogen assay" is any analytical test that can determine the concentration of urea in blood or other fluids.

The term "cartridge" refers to any container designed to contain a powder, fluid, or gas made for ready connection to a device, structure, system, flow path or mechanism. The container can have one or more compartments. Instead of compartments, the container can also be comprised of a system of two or more modules connected together to form the cartridge wherein the two or more modules once formed can be connected to a device, structure, system, flow path or mechanism.

A "chemical sensor" is a sensor that senses one or more variables based on the chemical properties of a component of a medium.

A "circular shape" describes a urease pouch constructed in a generally round shape having the form of a circle. This term is not intended to limit the shape of the urease pouch to any particular size or dimensions, and may encompass oval or oblong configurations as well.

A "compartment" means a part or a space designated, defined, marked or partitioned off from a structure. For example, a urease compartment in a sorbent cartridge is space defined within the sorbent cartridge containing urease. Optionally, the compartment can be in selected fluid communication with other compartments or modules of the sorbent system. The compartment can be physically separated or marked off without a physical barrier.

A "component" is any portion of a larger system. Non-limiting examples of components are containers, reservoirs, sensors, modules, and sorbents.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "container" as used herein is a receptacle that may be flexible or inflexible for holding any fluid or solid, such as for example a spent dialysate fluid, or a sodium chloride or sodium bicarbonate solution or solid, or urease, or urease/alumina, and the like. Generally, a container is a component of a larger system. A "sorbent container" is any receptacle configured to hold one or more sorbent materials. Similarly, a "urease container" is any receptacle configured to hold urease.

The term "contain" as used herein means to keep a material within a specific place. "Contain" can refer to materials that are placed within a compartment, absorbed onto a component, bound to a component, or any other method of keeping the material in a specific place.

"Dialysate" is the fluid that passes through the dialyzer on the side of the dialysis membrane that is opposite to the fluid (e.g. blood) that is being dialyzed.

"Dialysis" is a type of filtration, or a process of selective diffusion through a membrane. Dialysis removes solutes in the blood of a specific range of molecular weights via diffusion through a membrane from a fluid to be dialyzed. During dialysis, a fluid to be dialyzed is passed on one side of a filter membrane, while dialysate is passed on the other side of that membrane. Dissolved solutes are transported across the filter membrane by diffusion between the fluids. The dialysate is used to remove solutes from the blood being dialyzed. The dialysate can also provide enrichment to the other fluid.

A "disc-like shape" describes a urease pouch forming a flat, circular shape, as in a compressed cylinder. This definition is not intended to limit the dimensions or radius of the urease pouch, and may therefore encompass discs having an oval shape, and discs of any radial width or thickness.

A "double layer of material", "double layer of fabric" or "double layer" describes a second layer of material of the same or smaller area than the primary layer of material, disposed on the surface of the primary layer of material forming a surface of a urease pouch. The material used to form the double layer can be the same or different from the material forming the primary layer. Any rigid or flexible porous material known in the art is contemplated.

An "elastomer" or "elastomeric material" is a material comprising a polymer having high elasticity, such that the material may be easily stretched and shaped to be adapted to an internal cavity defined by a sorbent cartridge.

"Engagement members" allow compartments to cooperatively engage. In certain embodiments, these engagement members may be clasps or latches. In one embodiment, an engagement member allows for coupling of a top portion and a bottom portion of a urease pouch that can be opened and resealed.

An "exterior side" is a portion of a container or component that is on the outside of the container or component, as opposed to an "interior section" of a container or component, which denotes the inside of the container or component.

A "fixed amount" refers to an amount of sorbent material that cannot be changed during a particular dialysis session. However, the "fixed amount" as used in the context of the sorbent cartridge of the present invention can change from one dialysis session to another dialysis session, or from one patient to another patient. For example, a first dialysis session for a patient A at time X has a "fixed amount" of rechargeable sorbent materials while a second dialysis session for the same patient A at time Y can have a different "fixed amount" of rechargeable sorbent materials from the "fixed amount" at time X. Similarly, patient A can have a different "fixed amount" of sorbent materials from a patient B.

A "flexible structure" describes a urease pouch being formed of a porous material, wherein the urease pouch can be manipulated to fit an internal cavity defined by a sorbent cartridge.

"Flow" refers to the movement of a fluid or gas.

A "fluid" is a liquid substance optionally having a combination of gas and liquid phases in the fluid. Notably, a liquid, as used herein, can therefore also have a mixture of gas and liquid phases of matter.

The term "fluid communication" or "fluid connection" refers to the ability of fluid or gas to move from one component or compartment to another within a system or the state of being connected, such that fluid or gas can move by pressure differences from one portion that is connected to another portion.

A "fluid impermeable material" is any material through which fluid cannot pass.

The term "fluidly connectable" refers to the ability of providing for the passage of fluid or gas from one point to another point. The two points can be within or between any one or more of compartments, modules, systems, components, and rechargers, all of any type.

"Functional capacity" is the ability of a material to accomplish the material's intended function. In some instances functional capacity can refer to the ability of a sorbent material to remove specific solutes from a fluid, or to transform specific solutes into other materials.

"Hermetically sealed" refers to a seal that is airtight, or substantially impermeable to gases or fluids.

"Immobilized," as used to refer to a chemical component, refers to a configuration wherein a chemical component is held in place by some force. The force may be provided by absorption, adsorption, adhesion, or any other method for the chemical to be held in place.

The term "impregnated" describes any process known to a person of ordinary skill in the art by which a material may be caused to absorb or be saturated with a substance. In one embodiment, the material forming a urease pouch may be impregnated with an anticoagulant, such that the surface of the urease pouch absorbs the anticoagulant.

A "modular dialysate regeneration assembly" or "modular regeneration assembly" is one or more sorbent compartment containing at least one sorbent material attached to at least another sorbent compartment. The sorbent compartment can be the same or different size and/or contain different or the same amount of sorbent material.

"Module" or "modular" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. The designation of "first," "second," "third," etc. does not refer to the respective placement of the module in the direction of fluid or gas flow, but merely serves to distinguish one module from another unless otherwise indicated.

"Multi-use" refers to a section of a sorbent cartridge that can be recharged, as used herein, such that after recharging, the sorbent cartridge can be placed back into service for dialysis. A multi-use section of a sorbent cartridge requires recharging of the sorbent materials within the sorbent cartridge, but not necessarily replenishment of the sorbent materials.

An "optical sensor" is a sensor that senses one or more variables based on changes in the light emitted from, reflected from, absorbed by, or that travels through a medium.

The terms "pathway," "conveyance pathway," "fluid flow path," and "flow path" refer to the route through which a fluid or gas, such as dialysate or blood travels.

A "planar top" or "planar base" is a surface perpendicular to the axis of the urease pouch culminating at the uppermost portion of the upwardly extending walls of a urease pouch, or a flat surface culminating at the bottommost portion of the downwardly extending walls of a urease pouch, respectively. The planar top may be any geometric shape and dimensions complementary to the upwardly extending walls of the urease pouch, for example round, square, triangular or rectangular. A circular planar top or planar base is a flat surface having a circular shape, while a rectangular planar top or planar base is a flat surface having a square or rectangular shape.

The term "pore size" refers to a the size of a small interstice or hole admitting absorption or passage of liquid.

A "porous material" may describe any suitable porous material known in the art from which a urease pouch may be constructed. For example, the porous material can include, but is not limited to, bolting cloth, cotton, ashless filter paper, Dacron and polyethylene terephthalate. The porous material chosen for individual urease pouches may be selected based upon specific porosity in view of the sorbent material to be contained within the urease pouch.

"Recharging" refers to the process of treating a sorbent material to restore the functional capacity of the sorbent material, so as to put the sorbent material back into a condition for reuse or for use in a new dialysis session. In some instances, the total mass, weight and/or amount of "rechargeable" sorbent materials remain the same. In other embodiments, the total mass, weight and/or amount of "rechargeable" sorbent materials may change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a particular sorbent material such as urease. Notably, urease is not generally "recharged," but can be is replenished, as defined herein.

"Replenishing" means to add back into a system, section or module, a material that was previously removed, reduced, depleted, or taken out from that system, section or module. For example, after introducing an amount of a sorbent material, e.g., urease, that was reduced in quantity and/or functional capacity in a compartment, the compartment with the freshly introduced sorbent material can then be said to be "replenished."

"Reusable" refers in one instance to a material that can be used more than one time, possibly with treatment or recharging of the material between uses. Reusable may also refer to a cartridge that contains a material that can be recharged by recharging the material(s) contained within the cartridge.

A "rigid structure" describes a urease pouch being formed of inflexible material such that the urease pouch cannot be manipulated and reshaped to be adapted to an internal cavity defined by a sorbent cartridge, but instead maintains its shape.

A "section" refers to any portion of a larger component. A section can be referred to as a "first section," "second section," "third section," etc. to refer to any number of sections. The designation of "first," "second," "third," etc. does not refer to the respective placement of the section in the direction of fluid or gas flow, but merely serves to distinguish one section from another unless otherwise indicated. Additionally, each section can be optionally physically separated such as by a divider or wall; however, referring to a particular section does not necessarily require physical separation and can merely refer to a particular location in which a material is contained.

A "semi-rigid structure" describes a urease pouch having surfaces that can be flexed, but that are substantially rigid unless force is applied to cause the surfaces to flex.

A "sensor" is a component capable of determining the states of one or more variables in a system. In one embodiment, a sensor may be capable of sensing the presence and/or concentration of at least one compound in the fluid flowing through at least one urease pouch, using any means known in the art.

A "separator" is a layer of flexible or rigid material positioned within a urease pouch that divides the urease pouch into top and bottom portions, such that sorbent materials housed in the top and bottom portions, respectively, do not come in contact with each other. The separator is formed of a porous material such that spent dialysate or other liquid may flow between the top and bottom portions of the urease pouch through the separator, but such that the sorbent materials housed in the top and bottom portions of the urease pouch cannot pass through the separator.

A "sewn stitch" is a method of joining two surfaces together using a thread composed of any material known in the art.

"Single-use" refers to a component, compartment, or module that is not capable of being recharged as defined herein. Oftentimes, a single use compartment can be replenished, as defined herein, with at least one material, e.g., urease, such that the compartment may be used in another dialysis session, but remains "single use" in the sense that the material is only being replenished, and not recharged. When the single use compartment is no longer suitable for use in dialysis, the single use compartment may be discarded whereas a "rechargeable" compartment can be recharged and put back into operation.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular dialysate regeneration assembly wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

"Sorbent materials" are materials capable of removing specific solutes from solution, such as urea or urea byproducts.

"Spent dialysate" is a dialysate contacted with blood through a dialysis membrane and contains one or more impurities, or waste species, or waste substances, such as urea.

"Solid urease" refers to urease in the solid phase of matter. The solid urease can be in a block of solid urease or in powdered form.

A "square" or "rectangular" shape describes a urease pouch having four edges and four angles. This description is not intended to limit the size and dimensions of the urease pouch, and may therefore encompass urease pouches having corners with angles greater than or less than ninety degrees, and with edges of differing lengths with respect to each other.

The term "substantially retains" when referencing a urease pouch means that the urease pouch retains greater than 75% of the sorbent material inside.

A "triangular shape" describes a urease pouch having three edges and three corners, wherein the edges and corners may vary in length and degree individually and with respect to each other.

"Upwardly extending walls" and "perpendicularly extending walls" describe the surfaces extending radially outward from the top and bottom surfaces of a urease pouch. For example, in a urease pouch having a disc-like shape, the circular top and bottom portions of the urease pouch are connected by the rounded upwardly extending wall of the urease pouch. The upwardly extending walls may be of any shape or dimensions complementary to the corresponding top and bottom portions of the urease pouch. In the case of a triangular shaped urease pouch, the upwardly extending walls would extend from a bottom portion of the urease pouch and culminate at a vertex, in the absence of a top portion.

The term "urease compartment" or "urease container" refers to a defined space or partition of any kind made from any material adapted for containing urease.

The term "urease door," or "door," refers to a portion of a component such as a sorbent cartridge that can be opened, and the contents of the sorbent cartridge behind the door can optionally be replaced.

The term "urease injection port" refers to a temporary or non-temporary opening or passageway allowing for the entry of urease from one compartment to another.

A "urease introducer" is any component of a sorbent cartridge that allows, facilitates, or provides for an amount of urease to be added to a sorbent cartridge. The use of the term introducer is used in the broadest sense. For example, the urease introducer can be an inlet, a flow passageway, a tube, a tray that functions to introduce urease into a defined compartment, or any other means that facilitates the introduction of urease.

The term "urease pouch" refers to a structure that contains at least urease and optionally one or more other sorbent material, and can be constructed from a material that can allow fluid to freely pass through the urease pouch while keeping the sorbent material inside.

A "urea sensor" is a component capable of detecting the presence of, or concentration of, urea in a fluid.

The term "urease solution" refers to any aqueous solution being formulated by blending a solvent, such as water based solvent, and urease. The solution can have optional components such as buffering components.

The term "urease tray" refers to a drawer structure having a housing, generally being a sorbent cartridge, wherein the urease tray defines an interior volume defined therein that can be adapted to receive, for example, a urease pouch, module or loose sorbent material. The drawer can be "slideably movable," or a "slideable tray" with respect to the interior volume of the housing between a first closed position, wherein the compartments are enclosed within the interior volume, and a second open position, wherein the compartments are at least partially accessible. The "urease tray" can also optionally have a mechanism for controllably locking and/or sealing the drawer in the first closed position.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

Urease Introduction System

The first and second aspects of the invention allow a user to add an amount of urease, in solid or solution form, into a fluid flow path using a urease pouch containing urease. In any embodiment of the first or second aspects of the invention, the urease solution can be injected into the fluid flow path and can travel through the fluid flow path until the urease solution contacts the urease pouch. The urease can then be adsorbed by any known material known to bind urease such as alumina, silica, or combinations thereof, in the urease pouch, or contained by the urease pouch without the use of the binding material where the urease will stay for the duration of dialysis. The urease can be immobilized or bound by any known means or material known by those of ordinary skill such as electrostatic or enzymatic binding. The urease can further be bound by any intermolecular interaction such as van der Waals forces, or by adsorption. In any embodiment of the first or second aspects of the invention, a urease pouch containing urease can be added as necessary to the system. By adding fresh urease in this fashion, urease can be added to either open or closed sorbent systems. Further, the system can be used with a reusable sorbent cartridge. In other words, the sorbent cartridge can contain all non-water soluble, rechargeable components such as zirconium phosphate and alumina (excluding urease) inside the sorbent cartridge. Providing urease via a urease introducer wherein the urease travels into a urease pouch, or adding a fresh urease pouch to a sorbent cartridge, allows the sorbent cartridge to be shipped or stored without the urease or urease pouch present, while the urease or urease pouch can be added prior to use, during use, or after the sorbent cartridge is used. The adjustable aspect of urease introduction can reduce costs associated with the complexity and timing of manufacturing a sorbent cartridge containing a urease pouch. Notably, depending on such factors as the formulation and the storage state of the urease, the urease may have a limited shelf life. By adding the urease or urease pouch just prior to starting dialysis, the sorbent cartridge can be stored for long periods of time without problems to the urease.

Moreover, the sorbent cartridge can be replenished with fresh urease for each dialysis session wherein replenishing the urease in the sorbent cartridge can result in the recharging of alumina with urease in the sorbent cartridge for additional dialysis sessions. In particular, the recharging of sorbent materials, such as alumina or zirconium phosphate, describes the ability to restore or enhance the functional capacity of the material. For example, alumina or zirconium phosphate can be recharged and restored to functional capacity by passing a solution containing the appropriate amount of solutes over the alumina or zirconium phosphate during a recharging process. Similarly, a rechargeable section or module can be recharged by passing the necessary solution through the section or module to restore the functional capacity of the module or section. In contrast, a replenishable sorbent material, in which the functional capacity has been reduced, is required to be replenished as described herein.

In any embodiment of the first or second aspects of the invention, the "urease pouch" can contain urease, with or without zirconium phosphate. Zirconium phosphate is a rechargeable, expensive material as opposed to the cheaper urease. The urease can be replenished as explained herein. Zirconium phosphate, which can be recharged, as defined herein, does not need to be placed in the urease pouch, and can instead be positioned directly in a sorbent cartridge without the need for a urease pouch. Thereby, a single cartridge design can be provided to simplify design and reduce cost per session.

The urease in a urease pouch can be replenished as shown in FIG. 1. A second section of a sorbent cartridge can contain sorbent materials such as zirconium phosphate or zirconium oxide. A first section of a sorbent cartridge 1 can contain a disc-shaped urease pouch 2, which in any embodiment of the first or second aspects of the invention may contain alumina, silica, or combinations thereof, and in any embodiment of the first or second aspects of the invention may not contain alumina, silica or a combination thereof. The urease pouch 2 can be placed into the first section or a bottom portion of the sorbent cartridge 1. Fluid can enter the sorbent cartridge 1 through inlet 7 and exit through outlet 8. Urease can be injected into a urease injection port 3 through injection site 9, which can be placed in a fluid flow path before the urease pouch 2, such as on the inlet 7. The urease injection port 3 can be in fluid communication with the inlet 7 of the sorbent cartridge 1. A bottom-side of the urease pouch 2 can be constructed from a material that has a large enough mesh size to allow the urease to enter the urease pouch 2. A top-side of the urease pouch 2 can be constructed from a material with a mesh size small enough so that the urease cannot move out of the urease pouch 2 as explained herein. In any embodiment of the first or second aspects of the invention, the urease pouch 2 can contain alumina, silica, or a combination thereof, which can immobilize the urease after the urease enters the urease pouch 2. In any embodiment of the first or second aspects of the invention, the urease pouch can be constructed from a material with a mesh size large enough so that urease can move from the urease pouch and immobilized on a sorbent material, such as alumina, downstream of the urease pouch. Before, during, or after a dialysis session, or whenever the amount of urease in the first section of the sorbent cartridge 1 is reduced, the user can inject a fresh amount of urease into the first section of the sorbent cartridge 1 through injection port 3. The urease will travel from the injection port 3 into the urease pouch 2, where the urease will be immobilized by either the alumina, silica, or a combination thereof, within the urease pouch 2, or by the top of the urease pouch 2, which has a mesh size that is too small to allow urease to pass out of the urease pouch 2.

In any embodiment of the first or second aspects of the invention, the urease pouch can be present in the sorbent cartridge upstream of a layer or pouch containing activated carbon. This ensures that portions of the urease injected into the sorbent cartridge are not removed from solution by the activated carbon prior to reaching the urease pouch, where the urease can be immobilized by alumina, silica or a combination thereof within the urease pouch, or because the top portion of the urease pouch has a mesh size too small to allow the urease to pass out of the urease pouch. In any embodiment of the first or second aspects of the invention, the urease pouch can be downstream of the layer or pouch containing activated carbon. Urease can function in order to breakdown urea into ammonium and carbon dioxide, without the urease being bound to the alumina or silica, or contained within a urease pouch. Importantly, because urease is water soluble, the urease should bind to some hydrophobic material within the cartridge, or be immobilized in a urease pouch, so that the urease doesn't simply pass through the cartridge. Alumina or silica is generally used for this purpose, but any hydrophobic, non-water-soluble material could work for this purpose. In some cases, the urease can bind to the other sorbent materials within the cartridge, such as activated carbon, zirconium phosphate or zirconium oxide, without a reduction in urease activity. In any embodiment of the first or second aspects of the invention, the other sorbent materials, such as activated carbon, zirconium oxide or zirconium phosphate, can bind urease that migrates from the alumina or silica layer, or from the urease pouch, while the urease can remain active. In embodiments of the first or second aspects of the invention wherein the activated carbon layer is downstream of the alumina or silica layer, or downstream of the urease pouch, the activated carbon can act as a safety backup, to capture urease that migrates through the alumina or silica, or the urease pouch, and would otherwise leave the sorbent cartridge. In any embodiment of the first or second aspects of the invention, a carbon loaded filter pad with a pore size large enough to allow urease to pass through the filter can be placed upstream of the alumina or silica layer, or the urease pouch. The carbon loaded filter pad can help to distribute the fluid flow through the cartridge, and remove trace contaminants in the starting water that could degrade the functionality of the urease. In any embodiment of the first or second aspects of the invention, the carbon loaded filter pad can have a pore size small enough to capture the urease.

The functional amount of the urease may be reduced in several ways: (1) the functional amount of urease may be reduced if the urease is stripped off of the sorbent cartridge due to the recharging of other sorbent materials, (2) by leaching out during dialysis, or during maintenance of the sorbent cartridge, or (3) by modification or rearrangement of the urease structure to make the urease less active.

In any embodiment of the first or second aspects of the invention, the first section of the sorbent cartridge 1 can be adapted to receive urease through a urease door 4. The urease door 4 can be disposed on an exterior side of the sorbent cartridge 1. The urease door 4 provides access to an interior of the sorbent cartridge 1. The urease pouch 2 of FIG. 1 can be removed through urease door 4. The urease door 4 can be opened by pivoting the urease door 4 on hinge 5. A fresh urease pouch, either containing alumina, silica or a combination thereof, or with a top mesh size small enough to not allow urease to flow through, can be placed into the sorbent module through urease door 4. In any embodiment of the first or second aspects of the invention, the urease pouch may allow dissolved urease to flow out of the pouch where the dissolved urease can be immobilized by alumina, silica, or a combination thereof, downstream of the urease pouch. A correct amount of urease can then be injected into the injection port 3, as required before, after, or during a dialysis session. The urease, once injected, can travel through a fluid flow path via the inlet 7 and into the urease pouch 2. However, in any embodiment of the first or second aspects of the invention, the urease cannot migrate past the top-side of the urease pouch 2, and as a result the urease should stay within the urease pouch 2. In any embodiment of the first or second aspects of the invention, additional alumina, silica, or a combination thereof, in layers appurtenant to the urease pouch 2 can be added to reduce urease migration, sequester urease within the urease pouch 2 or immobilize the urease after flowing out of urease pouch 2.

In any embodiment of the first or second aspects of the invention, urease pouches or modules containing other sorbent materials may be included in the sorbent cartridge 1. In any embodiment of the first or second aspects of the invention with a urease door 4, the injection port 3 is not necessary. The user can simply insert a new urease pouch containing urease through the urease door 4, wherein the fresh urease pouch contains the necessary urease and so no injection is necessary.

Urease door 4 can be sealed by any known method in order to prevent leakage when closed and the sorbent cartridge 1 is in use. In any embodiment of the first or second aspects of the invention, an elastomeric material, such as an o-ring, can be placed on the urease door 4, the sorbent cartridge 1 or both in order to create a seal. In any embodiment of the first or second aspects of the invention, gaskets or grease can be used in order to seal the urease door 4 to the sorbent cartridge 1.

In any embodiment of the first or second aspects of the invention, an optional valve 10 can be placed downstream of the urease injection port 3. The valve 10 can control fluid access from the urease injection port 3 into the sorbent module 1. The valve 10 allows the system to control the amount of urease that can be injected into the sorbent cartridge, and also the timing of the urease injection.

In any embodiment of the first or second aspects of the invention, another layer containing alumina, silica or a combination thereof, without bound urease can also be positioned after the alumina or silica and urease layer 2 to prevent urease migration.

The sorbent materials, other than urease, can be recharged by passing a solution containing the appropriate amount of solutes through the sorbent cartridge. The urease, although potentially removed during this process, can then be replenished by introducing new urease through the urease injection port, or through adding a new urease pouch to the sorbent cartridge. This allows the urease within the sorbent cartridge to be fully replenished without the need to remove or disassemble the sorbent cartridge in order to refill the cartridge and respective modules or components with new urease. In any embodiment of the first or second aspects of the invention, the sorbent cartridge can be a single fixed, durable column that allows for recharging of all of the sorbent materials within the sorbent cartridge except for urease, and for addition of urease into the column. In this way, the sorbent cartridge does not need to be replaced in order to replenish the urease and recharge the alumina.

In any embodiment of the first or second aspects of the invention, the second section of the sorbent cartridge can be multi-use. That is, because in any embodiments of the first or second aspects of the invention, the sorbent materials within the second section of the sorbent cartridge can be recharged, the second section can be used multiple times without the need to replenish any of the materials. In contrast, the first section can be limited to single-use such that once the amount of urease within the first section has been reduced, the urease must be replenished.

Any method of injecting the urease solution into the urease injection port 3 is contemplated by this invention. For example, a user may fill a syringe with urease solution and discharge the syringe into the injection port 3. The urease injection port 3 may be covered by a septum, which can be pierced by the syringe. The septum can be made of re-sealable rubber, silicone, or any other suitable material. One of ordinary skill will appreciate that many types of injection ports can be used for the intended purpose of injecting urease solution. In any embodiment of the first or second aspects of the invention, the urease solution can simply be transferred by any suitable means into the urease injection port 3, and then pumped into the rest of the dialysis system using a system of pumps and actuators. In any such embodiments of the first or second aspects of the invention, the urease injection port 3 may be covered with a removable cap that can be removed prior to addition of the urease solution. In any embodiment of the first or second aspects of the invention, the dialysis machine can automatically inject the urease into the injection port 3. A urease solution can be provided for within the dialysis machine. Whenever the amount of urease within the sorbent cartridge is reduced, the machine can automatically inject fresh urease into the urease injection port 3. In any embodiment of the first or second aspects of the invention, the dialysis machine can meter in the correct amount of urease that is to be injected into the urease injection port 3.

In any embodiment of the first or second aspects of the invention utilizing a urease injection port, the urease injected can be a solution of urease. The invention is adaptable to a wide range of fluids. The fluid of the solution can be water, buffer, priming solution, or any other fluid capable of dissolving the urease.

In any embodiment of the first or second aspects of the invention, the sorbent module 1 can be part of a modular dialysate regeneration assembly. That is, other modules containing sorbent materials can be attached to each other. In any embodiment of the first or second aspects of the invention, the recharging of the sorbent materials in the module or modules that do not contain urease can be accomplished by simply replacing those modules. Dialysate regeneration refers to the process of treating spent dialysate, containing solutes removed from the patient's blood, with one or more sorbent materials in order to remove specific solutes, such as urea, and thereby generate dialysate that can be reused for dialysis.

In any embodiment of the first or second aspects of the invention, an optional urea detector 6 can be placed in the fluid flow path at some point after the urease layer of the sorbent module. A urea detector 6 can detect urea that has not been converted to ammonia and $CO_2$ by urease. Urea can indicate insufficient urease being present in the sorbent cartridges of the present invention and that more urease may be required to meet therapy goals. Moreover, urea can signal a need to add more urease into the sorbent cartridge, or urea may signal that the prior urease addition did not work properly. In any embodiment of the first or second aspects of the invention, the system may give the user an audio or visual alert if the urea detector detects urea in the spent dialysate after passing through the urease containing module. Without being limited to any particular method, there are two general methods for the measurement of urea nitrogen. The diacetyl, or Fearon, reaction develops a yellow chromogen with urea quantified by photometry. The reaction can be modified for use in autoanalyzers and can provide relatively accurate results. Enzymatic methods rely on an enzyme, which can convert urea to ammonia and carbonic acid. These products, which are proportional to the concentration of urea in the sample, can be assayed in a variety of systems, some of which are automated. One system checks the decrease in absorbance at 340 mm when the ammonia reacts with alpha-ketoglutaric acid. Other systems can measure the rate of increase in conductivity of the solution in which urea is hydrolyzed. Alternatively, urea can be measured indirectly by an ammonia detector located downstream of the urease layer and upstream of the zirconium phosphate layer. In general, low or no detected ammonia in fluid after passing through the urease layer but before reaching the zirconium phosphate layer can trigger an alert or workflow for adding fresh urease to a dialysis system. Any method of detecting the amount of urea that is converted to ammonia in the sorbent cartridge is contemplated by the invention. In addition to the methods above, the detection can be accomplished by any means known in the art, including but not limited to, the use of an optical sensor, a chemical sensor, a blood urea nitrogen assay, an ammonium sensor, or any combination thereof.

In any embodiment of the first or second aspects of the invention, an amount of urea converted to ammonia by the urease in a sorbent cartridge can be detected, such as by detecting the amount of ammonia or urea in the dialysate before and after passage of fluid through the sorbent cartridge. For example, a first fluid stream sample can be measured just prior to a sorbent cartridge, and a second fluid steam sample measured just after the sorbent cartridge. Any number of measurements can be taken such as an amount of ammonia present pre- and post-sorbent. In particular, if ammonia measurements indicate to one of skilled in the art that the zirconium phosphate has reached capacity, an alert can be triggered or a workflow initiated for introducing zirconium phosphate via any of the described methods and features described herein. One of ordinary skill will understand that detection of ammonia may not be an indication of the sufficiency or insufficiency of urea conversion. Rather, detection of ammonium post-sorbent can indicate that the zirconium phosphate has reached functional capacity. For example, low ammonia levels in the fluid post-sorbent cartridge can indicate that zirconium phosphate has reached functional capacity in the sorbent cartridge.

In any embodiment of the first or second aspects of the invention, a urea detector can detect ammonia in the system that can indicate that zirconium phosphate contained within the system has reached capacity. In any embodiment of the first or second aspects of the invention, the amount of ammonia produced can be a function of the zirconium phosphate capacity and the system can determine if zirconium phosphate is required by the system.

In any embodiment of the first or second aspects of the invention, the sorbent cartridges of the present invention can be adapted to receive an amount of urease that can be adjusted based on dialysis parameters. Any amount of urease may be injected or added as described herein in order to replenish the urease in the sorbent cartridge. Moreover, the replenishing step can be performed before, after, or during dialysis, or during priming of the system. If an amount or level of urease in the sorbent cartridge or dialysis system becomes insufficient or lower than required levels during a dialysis session, the present invention can replenish urease levels without halting the dialysis session. Critically, the adjustability of the amount of urease to be added in-session can provide flexibility in type of treatment delivered and therapy goals. The adjustable amount of urease can further provide for personalization of treatment and also result in a system that can be easily adapted to provide treatment for different patients. Adjustability in urease can reduce waste and tailor treatment to specific goals not possible with systems having not mechanism for adjusting an amount of urease being used during dialysis or across different treatment sessions.

An amount of urease required may be reduced by introducing the urease only when urease introduction is needed such as after priming of the system in preparation for use. One of ordinary skill can provide a specific amount of urease needed for a particular patient via prescription thereby customizing the amount of urease required to the specific patient. The amount of urease added can be based on the patient (size, weight, BUN, etc.). Such patient customization or prescriptions can be performed in lieu of a sensor-based system or in conjunction with such sensor-based systems. In particular, the sensor-based systems having sensors capable of providing feedback regarding an amount of urease contained in the system and provides an input to further adjust the amount of urease required. Urease can be added to the sorbent cartridge at any point, including before, during, or after a dialysis session.

Figure 2:
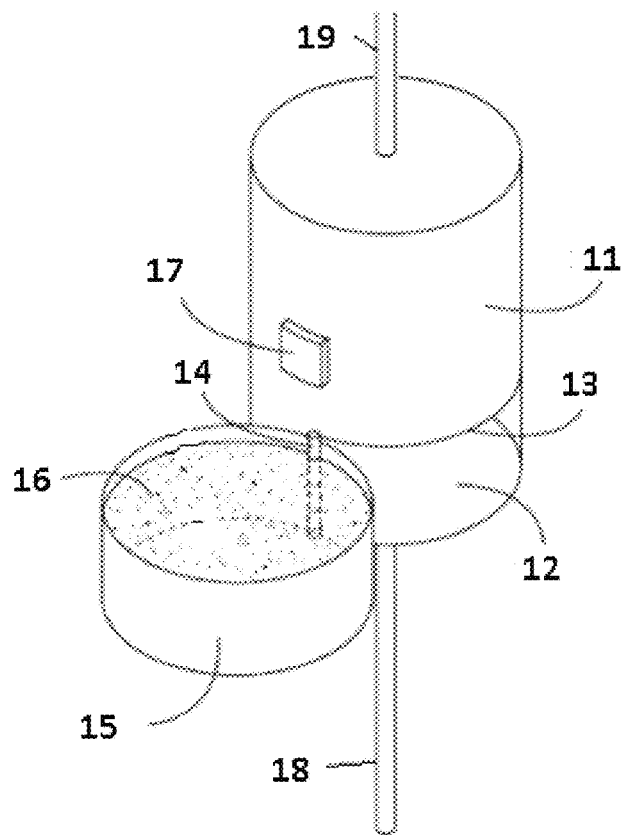
FIG. 2 shows a sorbent cartridge having a urease pouch and a urease tray.

In any embodiment of the first or second aspects of the invention, as shown in FIG. 2, a urease tray 15 can be included wherein the urease tray 15 is slideably removable from the sorbent module 11, or hingeably disposed on the sorbent module 11 by hinge 14. The urease tray 15 can be adapted to receive a urease pouch or solid urease as described herein. One skilled in the art will understand that any means of connection between the sorbent module 11 and urease tray 15 is within the scope of this invention, and that in any embodiment of the first or second aspects of the invention, hinge 14 is unnecessary. The urease tray 15 can have a length, width, and height to define an interior region for receiving solid urease or pouch of urease 16. In any embodiment of the first or second aspects of the invention, the urease tray 15 can be hermetically sealed to prevent contamination or leaking when closed. A hermetic seal can be created with the use of PTFE sealing rings, o-rings, grease or any other material known in the art capable of creating a hermetic seal disposed on the edges of urease tray 15.

The urease pouch or module is described herein. Fluid can enter the sorbent module 11 through inlet connector 18 and exit through outlet connector 19. The urease tray 15, in use, can fit into space 12 in the sorbent cartridge 11. The user can, whenever the amount of urease present in the sorbent module 11 has been reduced, place a new urease pouch or solid urease in the urease tray 16, and slide the urease tray into space 12. Optional urea detector 17 can detect urea in the fluid leaving the urease/alumina pouch 16. In any embodiment of the first and second aspects of the invention, alumina can be placed after the space 12 for the urease pouch 16 such as at the top of the space 13 in order to bind the introduced urease, or to prevent urease migration beyond the intended location.

Figure 3:
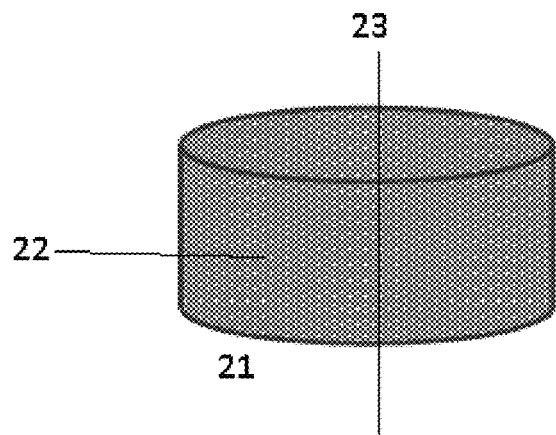
FIG. 3 shows a urease pouch containing urease.

A porous urease pouch can be used as the urease source in a sorbent cartridge, as shown in FIG. 3. The urease pouch 21 can be made as described herein, so that the alumina and urease 22 inside the urease pouch 21 cannot move through the urease pouch 21 and out of the sorbent module, but so that the spent dialysate can move freely through the urease pouch 21 to contact the urease inside. In any embodiment of the first or second aspects of the invention, the material can be selected with a mesh or pore size small enough to allow small molecules to pass through, but not allow free urease to pass through. Because in such embodiments the urease is kept within the urease pouch, the urease may react with the urea in the spent dialysate while the urease is in solution, which may eliminate the need for alumina to support the urease. In any embodiment of the first or second aspects of the invention, the pore size may be large enough to allow dissolved urease to flow through the pouch, where the urease can be immobilized by alumina within the sorbent cartridge downstream of the urease pouch. In any embodiment of the first or second aspects of the invention, jack bean urease can be used or other forms of urease, both naturally isolated or recombinant forms, known to those of ordinary skill. In any embodiment of the first or second aspects of the invention, the urease pouch can contain solid urease that can be dissolved by fluid that enters the urease pouch.

The urease pouch 21 in FIG. 3 is shown as a disk-shaped pouch. However, any of the described embodiments of the first or second aspects of the invention can be made in any shape, including a circular shape, a square shape, a triangular shape, a rectangular shape, a disc shape, a cylindrical shape, a spherical shape, a substantially rectangular shape, or a cubical shape. Each shape described can be substantially in the form described and can vary in dimensions without departing from the first or second aspects of the invention. For example, a pouch having a generally spherical shape, which is slightly ovoidal, is contemplated by the invention. Similarly, a disc having a tapered end on one or more ends to form a cone or being conoidal in form is also contemplated. Such variations from the generally described geometrical shapes are each encompassed by the invention. In any embodiment of the first or second aspects of the invention, the upwardly extending walls of the urease pouch 21 can slope inward toward axis 23, creating a urease pouch with a top surface having a smaller surface area than the bottom surface. In any embodiment of the first or second aspects of the invention, the upwardly extending walls can slope away from axis 23, creating a urease pouch with a top surface having a larger surface area than the bottom surface. In any embodiment of the first or second aspects of the invention, the upwardly extending walls can be parallel to axis 23, creating a urease pouch with a top and bottom surface area that are equal. In any embodiment of the first or second aspects of the invention, the size and shape of urease pouch 21 can be selected based on the size and shape of the interior portion of the sorbent cartridge, in order to provide a seal between the sorbent cartridge and the urease pouch 21 as described herein.

In any embodiment of the first or second aspects of the invention, the urease pouch may be constructed with a different pore size on the top of the pouch than on the bottom. For instance, the top of the urease pouch may be constructed with a pore size that will substantially retain the urease within the urease pouch. The bottom of the urease pouch can be constructed with a pore size that will allow dissolved urease to travel through the bottom of the urease pouch. In such embodiments of the first or second aspects of the invention, urease in solution can enter the urease pouch through the bottom of the urease pouch, but cannot exit the urease pouch through the top of the urease pouch.

Any useable concentration of urease within the urease solution to be added is within the scope of this invention. In any embodiment of the first or second aspects of the invention, the urease concentration can be between 10 mg/mL and 100 mg/mL. In any embodiment of the first or second aspects of the invention, the urease concentration can be between any of 1 mg/mL to 250 mg/mL, 15 mg/mL to 150 mg/mL, 10 mg/mL to 100 mg/mL, or 75 mg/mL to 250 mg/mL. One of ordinary skill can determine a range suitable for a particular patient or clinical outcome.

In any embodiment of the first or second aspects of the invention, the urease solution can be provided in a pre-packaged amount. Before a dialysis session, whenever the amount of urease within the urease module or pouch is reduced, or after recharging the other sorbent materials, the pre-packaged amount of urease can be added to the sorbent cartridge to ensure a fresh supply of urease within the sorbent cartridge. The pre-packaged amounts can be between 1.3 mL and 13.3 mL of urease solution with an activity of 300 unit/mg. In any embodiment of the first or second aspects of the invention, the pre-packaged amounts can be between any of 1.5 mL to 3.5 mL, 2.3 mL to 10.3 mL, or 5.0 mL to 12.3 mL or more. Indeed, the pre-packaged amounts can be in any suitable range of volumes or specific volume without limitation. In this manner, an amount of urease solution specific to a patient or desired clinical outcome can be added to a dialysis system prior to initiating a dialysis session or if urease levels are insufficient. In any embodiment of the first or second aspects of the invention, urease can be provided in a separate sorbent module or container having a proper amount of urease to be added. The separate sorbent module or container can ensure that the correct amount of urease is added to the sorbent cartridge conveniently and easily, thereby limiting the number of opportunities for user error and waste of sorbent materials. The separate sorbent module or container can be single or multi-use depending on the design and type of sorbent materials contained herein. For example, a sorbent module containing zirconium phosphate packaged together with a urease/alumina layer can be used multiple times, whereas a module only containing alumina and urease may only be designed for single-use. Based upon the patient or desired clinical outcome, the amount of urease can depend on the blood urea nitrogen (BUN) content of the patient's blood. For example, more urease can be added for patients with a higher BUN than for patients with a lower BUN. Moreover, overweight patients may need more urease than underweight patients.

If an amount of the urease within the sorbent cartridges of the present invention has been reduced, or prior to using a sorbent cartridge shipped without urease, a user can introduce the urease pouches and/or concurrently inject urease solution via the urease injection port, or replenish the urease pouch. In any embodiment of the first or second aspects of the invention, the system can prompt the user to introduce one or more fresh urease pouch(es) or a set of modular pouches per specified patient or therapy requirements into the sorbent cartridge before each dialysis session. The user prompts can also be generated after a set number of dialysis sessions, or whenever the amount of urease within the sorbent cartridge is insufficient. In any embodiment of the first or second aspects of the invention, the urease solution injected into the urease injection port can be of a higher concentration, and can be complimentary to the urease pouch. The injected urease solution can then be diluted by water as the solution flows in a fluid flow path into the sorbent cartridge. In any embodiment of the first or second aspects of the invention, the user need only remove the used urease pouch containing urease and insert the new urease pouch containing urease into the sorbent cartridge.

In order to test the effectiveness of urease solution injection for loading urease into a sorbent cartridge, such as with the urease injection port described herein, as opposed to loading urease to a column as a dry powder, several experiments were run. These experiments are described herein as Examples 1-4. Example 1 refers to the loading of urease onto a column using a dry powder loading procedure. Examples 2 and 3 are the analysis of the urease migration and urea conversion obtained from the dry powder loading procedure of Example 1. Example 4 relates to the loading and analysis of urease onto a column using a urease solution.

EXAMPLE 1

An Ace Glass 25 millimeter Adjusta-Chrom Jacketed Column (P/N 5819) was packed with a mixture of 3.001 grams activated alumina (Shandong Luye Co, Lot 20140811-1) and 0.0040 grams of purified urease (Tokyo Chemical Industry, Lot P7DWG-TJ). An additional 9.0070 grams of activated alumina (Shandong Luye Co, Lot 20140811-1) was added to the column and the outlet frit and plunger were adjusted so that no dead space existed above the alumina layer and locked into place. Heated water was circulated through the external jacket of the column to maintain a temperature of 37° C. throughout the experiment. The column was primed by pumping base buffer (115 mMol sodium chloride and 25 mMol sodium bicarbonate) at 15 ml/minute until the liquid level reached the top of the alumina then held for five minute without flow to allow the urease to distribute and bind to the alumina. After the hold period the priming solution flow was restarted at 15 ml/min for an additional 5 minutes to complete the priming sequence. When the priming sequence was completed the column feed was changed to a test solution containing 25 mMol/Liter of urea (Sigma Aldrich) in base buffer. The flow rate was maintained at 15 mL/min for 60 minutes. The column effluent was collected for urease migration analysis and separate 8 mL samples were collected after 10, 30 and 60 minutes of test solution flow for urease conversion testing.

EXAMPLE 2

A urea challenge solution was made containing 400 mMol/Liter phosphate buffer and 400 mMol/L urea. A 1.8 mL sample from the pooled column effluent from Example 1 was mixed with 1.8 mL of the urea challenge solution and incubated at room temperature for 10 minutes. Ammonium levels in the solution were measured using a Nova BioProfile 300 analyzer every 10 minutes over a period of 50 minutes. The ammonium concentration was plotted as a function of time and a linear regression was performed to determine the urease activity of the solution. The urease activity was then multiplied by the total volume of effluent run through the column to determine the total urease units (IU) that migrated during the test. For Example 1 the result was 53 International Units of migrated urease.

EXAMPLE 3

The test samples collected at 10, 30 and 60 minutes in Example one were used for this analysis. A 0.8 mL aliquot of test sample was mixed with a 0.8 mL aliquot of 400 mM/L phosphate buffer and mixed vigorously. The ammonium concentration was determined using the Nova BioProfile 300 analyzer using the automated machine procedure. The results were compared to a standard curve measure in the same way using standard of known concentration. The ammonium concentration in the test sample is used to calculate the percent urea conversion for the urease/alumina reactor. For Example 1 the result was 53.4% urea conversion.

EXAMPLE 4

The test system of Example 1 was modified to include a three way valve in the inlet feed line. The three way valve had one port compatible with a luer lock syringe and the other ports connected to the test solution and test column inlet. The Ace Glass 25 millimeter Adjusta-Chrom Jacketed Column was packed with 12.001 grams of alumina (Shandong Luye Co, Lot 20140811-1). A solution of 0.0079 grams urease (Tokyo Chemical Industry, Lot P7DWG-TJ) was mixed in 8.0 mL of base buffer (115 mMol sodium chloride and 25 mMol sodium bicarbonate) to make a solution of approximately 300 IU/mL. The urease was charged into the reactor by injecting 1.3 mL of base buffer, followed by 4.0 mL of urease solution and 1.8 mL of base buffer. The base buffer was used to fill the inlet line before introducing the urease and to ensure all the urease was flushed out of the inlet feed line and into the alumina. After introduction of the urease, the column was tested according to the method described in Examples 2-3. The urease migration for this test column was 47 International Units and the urea conversion was 67.4%.

The results of the experiments in Examples 1-4 are summarized in Table 1. As can be seen in Table 1, the results obtained from the urease solution loading were comparable to the results obtained with dry powder loading. Although additional experiments will be necessary to determine the superiority of one method over the other, the results demonstrate that a liquid load is possible without all of the enzyme migrating out of the column.

TABLE 1

| Method of Urease Loading | Urease Migration | Urea Conversion |
| --- | --- | --- |
| Dry Powder Loading (Example 1) | 53 IU | 53.4% |
| Urease Solution Loading (Example 4) | 47 IU | 67.4% |

Sorbent Dialysis

Figure 4:
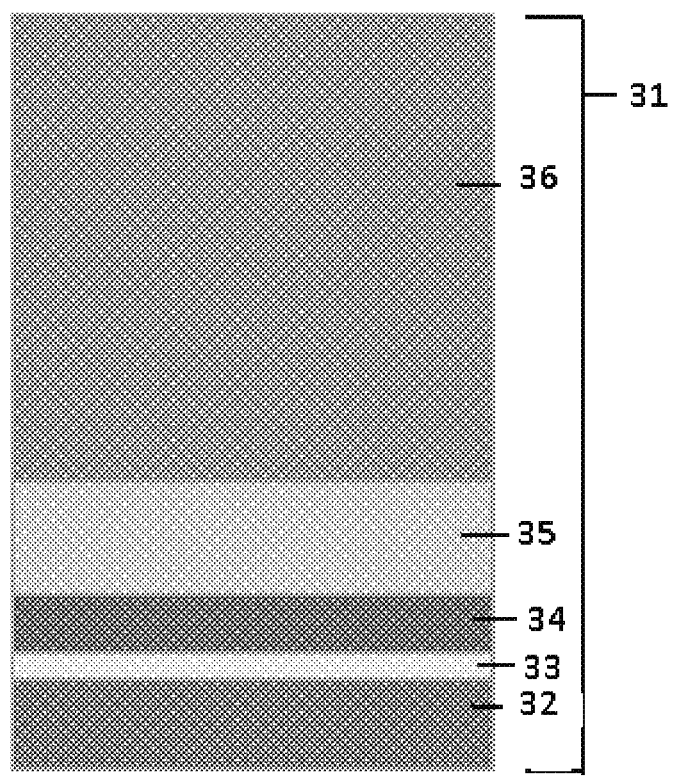
FIG. 4 shows an exemplary embodiment of a sorbent cartridge.

One non-limiting exemplary sorbent cartridge is shown in FIG. 4. Spent dialysate or fluid can flow from the bottom of the sorbent cartridge 31 to the top of the cartridge. The first sorbent material the spent dialysate or fluid contacts can be activated carbon 32. Activated carbon 32 will remove non-ionic toxins from the fluid by adsorption. Creatinine, glucose, uric acid, β2-microglobulin and other non-ionic toxins, except urea, can be adsorbed onto the activated carbon, removing those toxins from the fluid. Other non-ionic toxins will also be removed by the activated carbon. The dialysate or fluid then continues through the sorbent cartridge 31 to the alumina and urease layer 33. The fluid can then move through the sorbent cartridge 31 into the hydrous zirconium oxide layer 34. The hydrous zirconium oxide layer 34 can remove phosphate and fluoride anions, exchanging them for acetate anions. Alternatively, the layers 33 and 34 can be reversed wherein dialysate flows through the sorbent cartridge 31 first to the hydrous zirconium oxide layer now positioned at 33, and then continue to move through the sorbent cartridge 31 into the alumina and urease layer now positioned at 34.

Urease can catalyze the reaction of urea to form ammonia and carbon dioxide. The result of this reaction is the formation of ammonium carbonate. The phosphate anions present in the fluid can also be exchanged for hydroxide ions on the alumina. As the fluid continues through the sorbent cartridge 31 in FIG. 4, the fluid reaches an optional alumina layer 35. The optional alumina layer 35 can remove any remaining phosphate ions from the fluid and help retain urease within the sorbent cartridge 31, and in certain configurations this layer 35 can exchange urea for ammonium and other components. The last layer through which the fluid travels can be the zirconium phosphate layer 36. In the zirconium phosphate layer 36, ammonium, calcium, potassium and magnesium cations can be exchanged for sodium and hydrogen cations. Ammonium, calcium, potassium and magnesium ions all preferentially bind to the zirconium phosphate, releasing the hydrogen and sodium ions originally present in the zirconium phosphate layer 36. The ratio of sodium to hydrogen ions released depends on the ratio originally present in the zirconium phosphate layer 36, and is therefore controllable. The result of the fluid passing through the sorbent cartridge 31 is that the fluid can be regenerated and form clean dialysate that can be safely passed back through a dialyzer to a patient. In any embodiment of the first or second aspects of the invention, potassium, calcium, and magnesium can be added to the clean dialysate to replace any ions which were removed by the sorbent cartridge. The ions can be added and or controlled via an infusate system that can be positioned on a section of the fluid flow path after the sorbent cartridge.

In any embodiment of the first or second aspects of the invention, the layers, 32, 33, 34, and 35 can comprise a second section of a sorbent cartridge that can be detached from a first section of the sorbent cartridge comprising layer 36 containing zirconium phosphate. The detached or detachable section(s) can be separated from a system, module, cartridge or any component of the sorbent cartridges of the present invention. The detachable components can be connected by any suitable means wherein the section can be taken out of a larger system with minimal time or effort. The detached component, section, or module can be optionally reattached to the system, module, cartridge or other component.

In any embodiment of the first or second aspects of the invention, the sorbent materials, other than alumina, can be recharged by passing a fluid containing the correct solutes through the material. For example, zirconium phosphate can be recharged by passing a fluid containing hydrogen and sodium ions through the zirconium phosphate. The hydrogen and sodium ions will replace the ammonium, potassium, calcium, magnesium or other ions removed by the zirconium phosphate during dialysis, and thereby place the zirconium phosphate back in condition to be used in sorbent dialysis. Zirconium oxide can be recharged by passing a solution containing acetate ions through the zirconium oxide. The activated carbon can be recharged by passing heated water through the activated carbon. The amount of each of the solutions that must be passed through the respective sorbent materials depends on the amount of sorbent material used. This process may strip the urease from the alumina, necessitating replenishment of the urease. In any embodiment of the first or second aspects of the invention utilizing alumina or silica as described herein, the step of replenishing the urease in the system can result in recharging of the alumina or silica.

Urease Pouches

The first and second aspects of the invention can utilize separate urease pouches that contain urease. Optionally, the urease pouches can contain individual layers of other sorbent material, or multiple layers of sorbent material. Spent dialysate or water may pass through the urease pouch and into the urease or other optional sorbent materials within. The first and second aspects of the invention can utilize separate urease pouches that contain individual portions of sorbent material, or multiple layers of sorbent material. The urease pouches can be formed from a porous material wherein the urease pouches contain at least one sorbent material. The porous material can allow fluid to pass through the urease pouches but substantially retains the urease in the urease pouch. In any embodiment of the first or second aspects of the invention, the porous material can allow fluid to pass through the urease pouches but can retain at least 98% by weight of urease in the urease pouch. In any embodiment of the first or second aspects of the invention, the porous material can allow fluid to pass through the urease pouches but can retain anywhere from at least 70%, 75%, 80%, 85%, 90%, 92%, 93%, 94%, 95%, 96%, or 97% by weight of urease in the urease pouch.

The urease pouches can be constructed in any shape. For convenience, they are often drawn as circular or disc shaped. However, any of the described embodiments of the invention can be made in any shape, including a circular shape, a square shape, a triangular shape, a rectangular shape, a disc shape, a cylindrical shape, a spherical shape, a substantially rectangular shape, a cubical shape, etc. In any embodiment of the first or second aspects of the invention, the shape of the urease pouch can be selected based on the shape of the interior of the sorbent cartridge.

Figure 5:
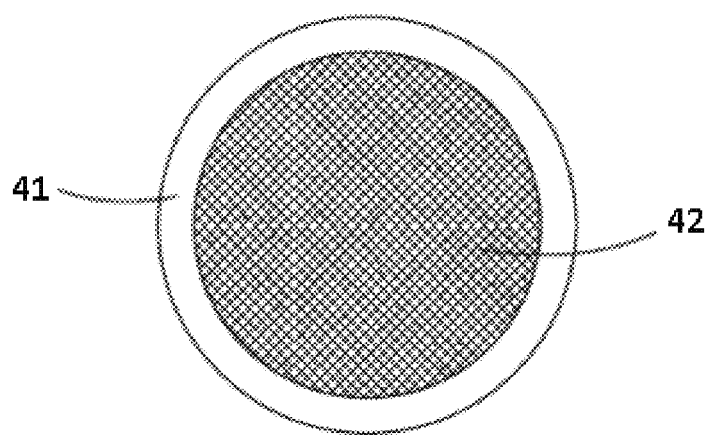
FIG. 5 is a top view of a disc-shaped urease pouch.
Figure 6:
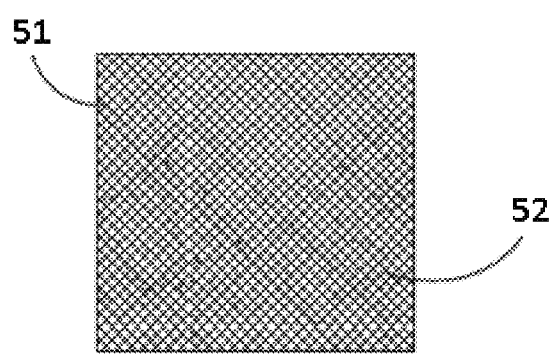
FIG. 6 is a front view of a rectangular-shaped urease pouch.
Figure 7:
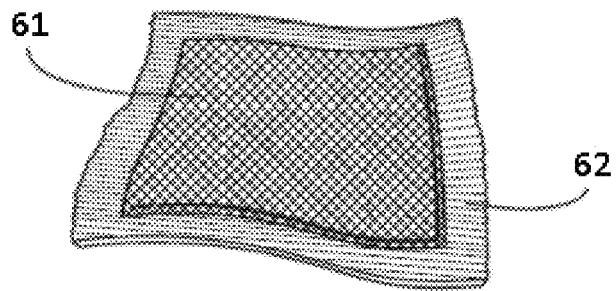
FIG. 7 is a perspective view of a rectangular urease pouch.

For example, FIG. 5 depicts a disc-shaped urease pouch 41 containing sorbent material 42, whereas FIG. 6 shows a rectangular-shaped urease pouch 51 containing sorbent material 52, and FIG. 7 shows a rectangular urease pouch 61. The urease pouches may be constructed of any known material, including filter paper, cloth, nylon, porous polymer and metal as described herein, and each may be constructed in any shape. In any embodiment of the first or second aspects of the invention, the urease pouch can contain a mixture of urease and alumina.

In any embodiment of the first or second aspects of the invention, the urease pouches can be configured as shown in FIG. 5. The urease pouch 41 can be constructed of a material that can allow fluid to pass through the urease pouch 41, but will not allow urease 42 contained within the urease pouch 41 to pass out of the urease pouch 41. The urease can be placed loosely in the urease pouch, allowing the urease to move within the urease pouch, but not to travel out of the urease pouch. The urease pouch can be made in any size or shape. In any embodiment of the first or second aspects of the invention, as shown in FIG. 6, the urease pouch 51 can be roughly rectangular shaped. In any embodiment of the first or second aspects of the invention, as shown in FIG. 5, the urease pouch 41 can be disc-shaped. In any embodiment of the first or second aspects of the invention, the urease pouch can be shaped to be adapted into an internal cavity defined by a sorbent cartridge. In this way, the urease pouch may fit in the space, such that there may be void space, but such that the urease pouch generally fits the space. For example, a sorbent cartridge having a cylindrical internal cavity can accommodate a circular or disc-shaped urease pouch, while a sorbent cartridge having a conical internal cavity could accommodate a triangular urease pouch, and a sorbent cartridge having a square or rectangular internal cavity could accommodate a square or rectangular-shaped urease pouch.

FIG. 7 shows a rectangular urease pouch embodiment in which the urease is contained in a raised inner portion of the urease pouch 61, while the outer perimeter of the urease pouch 61 having a finished or serrated edge 62 is sealed by any means known in the art, including heat or pressure stamping, sewing, or adhesive sealing. The finished or serrated edge 62 of the urease pouch 61 may be permanently sealed, or may alternatively be resealable, such that the urease pouch 61 may be opened and reclosed. For example, the finished or serrated edge 62 may be sealed with a resealable adhesive, hook and loop fasteners (not shown), or with interlocking ridges (not shown) that may be separated and reclosed by the user. Optionally, a latch member (not shown) may be included on the finished or serrated edge 62 of the urease pouch 61 to provide additional strength in sealing the urease pouch 61. In any embodiment of the first or second aspects of the invention, the outer edge may simply be a folded edge. In use, compression from the other materials within a sorbent cartridge can keep the folded edge sealed and the sorbent materials inside the urease pouch 61. Alternatively, the urease pouch 61 may be sealed with drawstrings that when tightened create a seal. In any embodiment of the first or second aspects of the invention, the edges of the urease pouch 61 need not be serrated. Any method of creating a sealed urease pouch is contemplated by this invention. The edges of the urease pouches can be simply woven together, sealed by adhesive, or closed by any other fashion known in the art.

The size of the urease pouches used in the invention is flexible. Because different amounts of each sorbent material may be required for a dialysis session, the urease pouches of the present invention may be in multiple sizes. In any urease pouch, glass beads can be incorporated into the sorbent material to facilitate flow.

The urease pouches may be constructed of a flexible structure, a rigid structure, or a semi-rigid material. In any embodiment of the first or second aspects of the invention, the urease pouches may be constructed out of both a flexible and a rigid material. For example, the top and bottom of the urease pouch may be constructed from a flexible material, while the sides of the urease pouch may be constructed from a rigid material. In any embodiment of the first or second aspects of the invention, the sides of the urease pouches can be fluid impermeable, while the top and bottom of the sorbent pouch can be permeable to fluid. In any embodiment of the first or second aspects of the invention, the urease pouches can be made out of a material such as a porous polymer. The polymer may be made porous by creating small holes or pores in an otherwise solid polymer material. In embodiments of the first or second aspects of the invention where the urease pouch is made of fabric, the weave of the fabric can have a specified porosity suitable for use the sorbent material described herein for the intended use of dialysis. The polymer may be constructed from polyethylene terephthalate, high density polyethylene, low density polyethylene, polyvinyl chloride, polypropylene, polystyrene, or any other polymer known in the art. The pores of the urease pouch material must be large enough to allow the spent dialysate to freely travel into and out of the urease pouch; while at the same time must be small enough to keep the particles of the urease inside the urease pouch to minimize urease migration. For this reason, urease pouches with different pore or mesh sizes can be utilized for different material layers. In any embodiment of the first or second aspects of the invention, the urease pouch may be made out of a natural fiber, such as cotton. In any embodiment of the first or second aspects of the invention, the urease pouch may be constructed from ashless filter paper. The urease pouches may also be constructed out of a synthetic material such as Dacron, or polyethylene terephthalate.

Figure 8A:
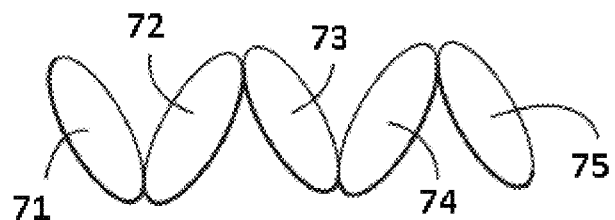
FIG. 8a is a side view of a string of disc-shaped urease pouches.
Figure 8B:
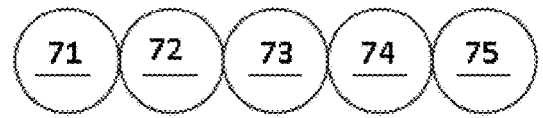
FIG. 8b is a top view of a string of disc-shaped urease pouches.
Figure 8C:
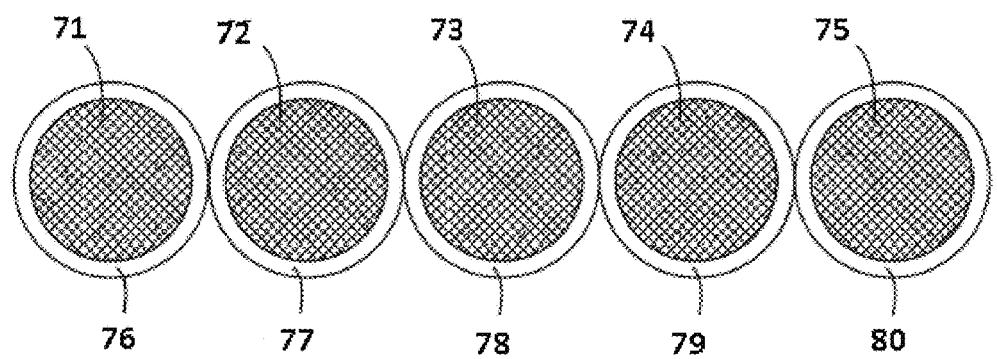
FIG. 8c is a side view of a string of disc shaped urease pouches connected by their edges.
Figure 8D:
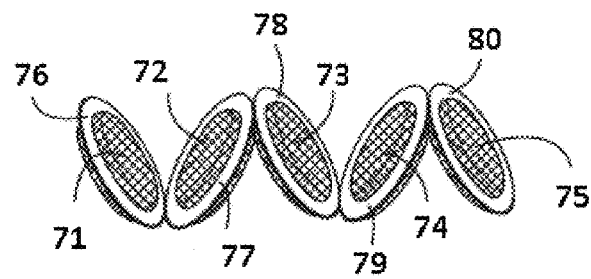
FIG. 8d shows a top view of a string of disc shaped urease pouches connected by their edges.

In any embodiment of the first or second aspects of the invention, multiple urease pouches may be connected as a string of urease pouches, as shown in FIGS. 8*a*, 8*b*, 8*c*, 8*d*, 9*a*, 9*b* and 9*c*. For example, as shown in FIG. 8*a* and FIG. 8*c*, the individual urease pouches 71-75 may be permanently or separably connected at their outer edges 76-80 in the case of the disc shaped urease pouches of FIG. 8*c* and the outer edges 86-90 of urease pouches 81-85 in the case of rectangular urease pouches of FIG. 9*c*, by any means known in the art, including by perforations in the material forming the outer edges 76-80 and 86-90. The materials of which the individual urease pouches are composed may be selected with particularity to urease. For example, urease has a molecular weight of between 480 kDa and 545 kDa. As such, the urease pouch can be constructed from a material that will not allow molecules with a molecular weight of between 480 kDa and 545 kDa to pass through. Any combination of urease pouch materials and mesh sizes among the string of urease pouches, and any number of individual urease pouches making up the string of urease pouches, is envisioned. Additionally, the interior portion of the urease pouches may be constructed in any shape, including but not limited to, rectangular or circular.

Figure 10:
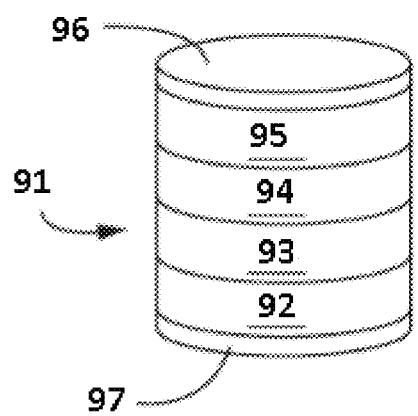
FIG. 10 is a side view of a sorbent cartridge containing activated carbon, hydrous zirconium oxide, urease, alumina, and zirconium phosphate.

One non-limiting embodiment of the urease pouches of the first and second aspects of the invention is shown in FIG. 10. The sorbent cartridge 91 can comprise multiple sorbent pouches, including a sorbent pouch containing activated carbon 92, a sorbent pouch containing hydrous zirconium oxide 93, a sorbent pouch containing alumina and urease 94, and a secondary sorbent pouch containing alumina 95. In any embodiment of the first or second aspects of the invention, alumina can be contained in one sorbent pouch and the urease in another sorbent pouch. Spent dialysate can enter through the bottom surface 97 of the sorbent cartridge 91, and flow through each of the sorbent pouches sequentially, and then flow out of the sorbent cartridge 91 through the top surface 96 of the sorbent cartridge 91. In this way, the spent dialysate can come into contact with each material layer, while each material layer is kept separate from each of the other layers. One skilled in the art will understand that the pouches may be arranged in alternate orders and still be within the scope of the invention. For example, in any embodiment of the first or second aspects of the invention, the first sorbent pouch may contain activated carbon, the second sorbent pouch may contain alumina and urease, the third sorbent pouch may contain hydrous zirconium oxide, and the fourth sorbent pouch may contain a second layer of alumina. In any embodiment of the first or second aspects of the invention, the first sorbent pouch may contain activated carbon, the second sorbent pouch may contain alumina and urease, the third sorbent pouch may contain a secondary alumina layer and the fourth sorbent pouch may contain hydrous zirconium oxide. Additionally, any number of sorbent pouches arranged sequentially in the sorbent cartridge is envisioned.

Figure 11A:
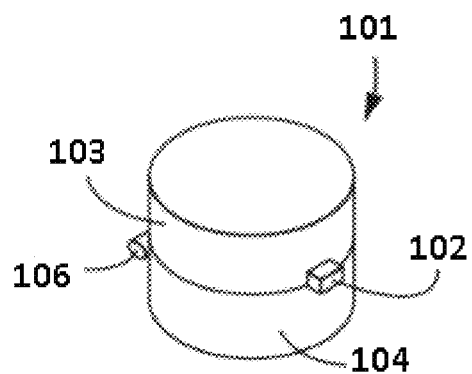
FIG. 11a is a perspective view of a urease pouch having the ability to open.
Figure 11B:
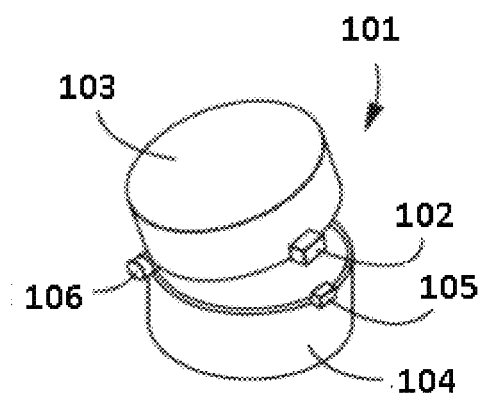
FIG. 11b is a perspective view of a urease pouch in an open state.

In any embodiment of the first or second aspects of the invention, the urease pouches may be designed so that they can be opened, as shown in FIG. 11*a*. Top portion 103 of the urease pouch 101 and bottom portion 104 of the urease pouch 101 may be connected by a hinge 106 and a latch member 102. When latch member 102 on the top portion 103 of urease pouch 101 is engaged with flange 105 on bottom portion 104 of the urease pouch 101, the top portion of the urease pouch 103 can be firmly sealed to the bottom portion of the urease pouch 104. When latch member 102 of the urease pouch 101 is disengaged from flange 105, top portion 103 can pivot on hinge 106 to separate from bottom portion 104. The remaining residue or material such as alumina within the urease pouch 101 can then be removed in order to be discarded or recycled. The urease pouch 101 itself may be reused. The urease pouch can be closed as shown in FIG. 11*b* by pivoting the top portion 103 of the urease pouch 101 so that top portion 103 and bottom portion 104 meet, and reengaging latch member 102 on the top portion 103 of the urease pouch 101 with flange 105 on the bottom portion 104 of the urease pouch 101. Any type of connection between the top portion 103 and bottom portion 104 of the urease pouch 101 is contemplated by the invention. For example, the top portion 103 of the urease pouch 101 may include multiple latches (not shown) in the absence of a hinge member, while the bottom portion 103 of the urease pouch 101 can include engagement members. When the top portion 103 is placed onto the bottom portion 104 and twisted, latches can engage the engagement members creating a connection that can be resistant to inadvertent opening. In order for the connection to be broken, the top portion 103 of the urease pouch 101 can be twisted in the opposite direction, allowing the two portions to separate.

In any embodiment of the first or second aspects of the invention, the urease pouches may be constructed so that they cannot easily be opened. In such embodiments of the first or second aspects of the invention, the urease pouches can be completely sealed to form a complete enclosure around the sorbent material. During construction of the urease pouch, once the sorbent material is added, the urease pouch can be sealed by any possible means. The urease pouches can be heat sealed to fuse the edges of the urease pouch together. Alternatively, an adhesive may be used to connect the edges together. In embodiments of the first or second aspects of the invention where a fiber is used to construct the urease pouches, the edges may be sewn or woven together with a sewn stitch to create a sealed urease pouch. Any type of chemical or mechanical closure to form the urease pouches is contemplated by this invention.

Figure 12A:
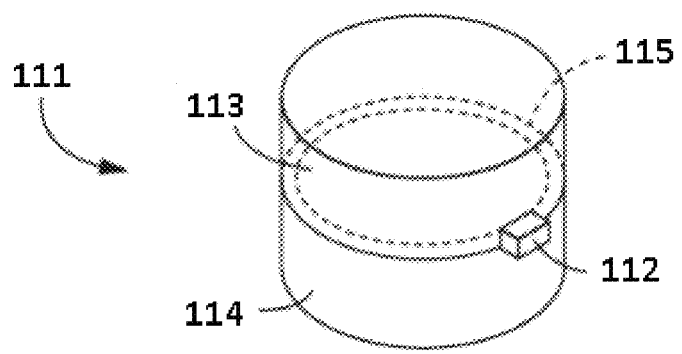
FIG. 12a is a perspective view of a rigid or semi-rigid urease pouch with an interior seal member.
Figure 12B:
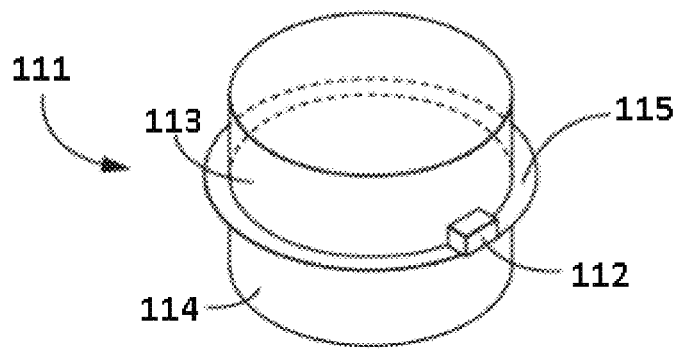
FIG. 12b a perspective view of a rigid urease pouch with an exterior seal member.

In any embodiment of the first or second aspects of the invention, the urease pouches may be made out of rigid material as shown in FIGS. 12*a* and 12*b*. The rigid urease pouch 111 can have latch member 112 to allow connection and detachment of the top portion 113 of the urease pouch 111 from the bottom portion 114 of the urease pouch 111. This facilitates the recycling or discarding of residue or leftover sorbent material such as alumina inside the urease pouch 111 while allowing the rigid urease pouch 111 to be reused. An interior ring or exterior ring 115 may be disposed inside or around the urease pouch 111, respectively, creating an additional internal or external sealing member to secure the top portion of the urease pouch 113 to the bottom portion of the urease pouch 114. The coupled surfaces of the rings may be covered in an adhesive material, or the rings may be attached by any other known coupling means. In any embodiment of the first or second aspects of the invention, the rings may be welded. In any embodiment of the first or second aspects of the invention, the rings may be mechanically attached to the urease pouches such as with rivets, screws or clamps. In any embodiment of the first or second aspects of the invention, engagement hooks may be placed on the rings, wherein the engagement hooks can attach to the urease pouch in a similar fashion as described for connecting the top and bottom portions in FIGS. 11*a* and 11*b*.

Figure 13:
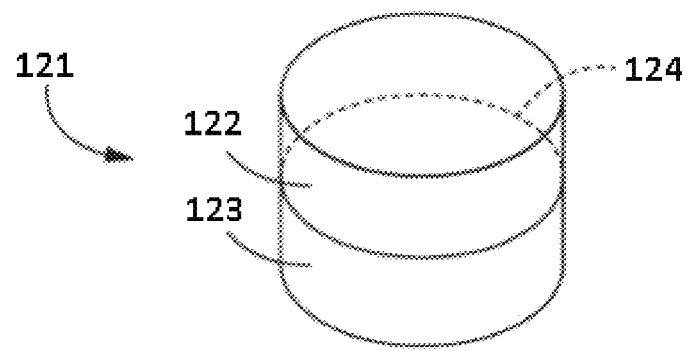
FIG. 13 is a perspective view of a urease pouch with an internal separator.

In FIG. 13, a single urease pouch can contain multiple sorbent materials. Urease pouch 121 can comprise a separator 124 within the urease pouch. The separator 124 can run through the entire interior space of the urease pouch 121. The separator 124 creates, within the urease pouch 121, a top portion 122 and a bottom portion 123, which are kept completely separate from each other. One sorbent material may be placed in the top portion of the urease pouch 122, and a different sorbent material may be placed in the bottom portion of the urease pouch 123. This allows two different materials to be placed within a single urease pouch, but remain separate from one another. In any embodiment of the first or second aspects of the invention, two or more sorbent materials can be placed in a single urease pouch without a separator. The sorbent materials may be arranged in layers within the urease pouch, or intermixed. The separator 124 can be constructed from the same material as the urease pouch itself, or may be a different material that still allows fluid to pass through the separator freely, while preventing passage of the sorbent material.

In any embodiment of the first or second aspects of the invention, more than one separator can be used within a single urease pouch. The present invention contemplates urease pouches containing 2, 3, 4 or more separators within a single urease pouch. In any embodiment of the first or second aspects of the invention, multiple sorbent materials can be mixed within a urease pouch. Mixing different sorbent materials together can be accomplished without a loss in efficiency of the sorbent materials.

Figure 14:
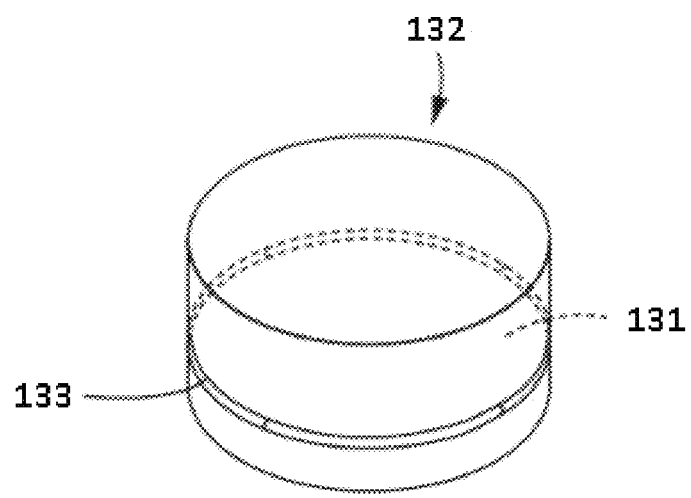
FIG. 14 is a perspective view of a urease pouch with an o-ring seal member.

The urease pouches of the first and second aspects of the invention can have a mechanism to create a seal between the urease pouch and the inner surface of the sorbent cartridge in which the urease pouch is placed, such that fluid is kept from flowing around the urease pouch and instead is directed into the urease pouch. FIG. 14 shows one non-limiting embodiment of a seal mechanism of the first and second aspects of the invention. A flexible urease pouch 131, such as one made out of a fiber, can be placed inside of a sorbent cartridge 132. In any embodiment of the first or second aspects of the invention, the urease pouch may be made out of a rigid material, such as a polymer or metal. In order to avoid a situation where spent dialysate flows around the urease pouch and therefore does not contact the sorbent material inside, the urease pouch 131 may be sealed to the sorbent cartridge 132. O-ring 133 placed on the circumference of urease pouch 131 can form a seal with the sorbent cartridge 132 so as to prevent spent dialysate from flowing around the urease pouch 132, and instead through the urease pouch 131. The urease pouch 131 may be filled so that the circumference of the urease pouch 131 is slightly wider than that of the sorbent cartridge 132. This will ensure that the urease pouch 131 covers the entire area of the sorbent cartridge 132 and that there are no spaces for fluid to pass by without flowing through the urease pouch 131. O-ring 133 can also serve to ensure that urease pouch 131 keeps the intended shape by providing a semi-rigid border.

Figure 15:
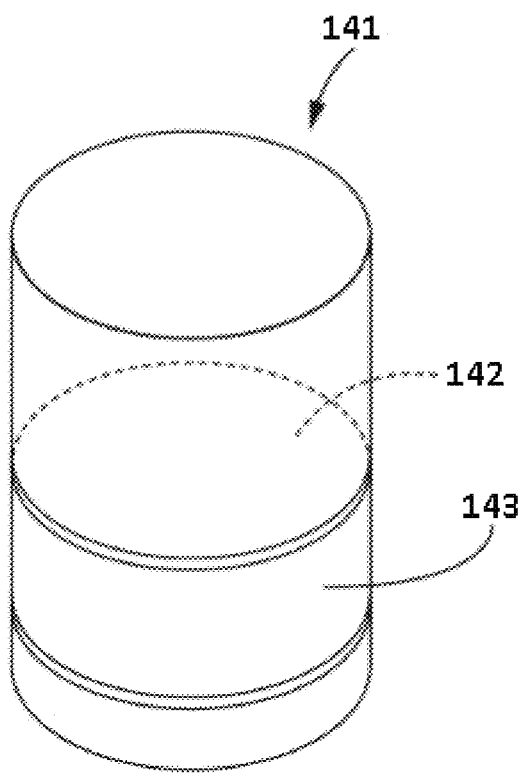
FIG. 15 is a perspective view of a urease pouch with an elastomeric material disposed on the side of the urease pouch.

In any embodiment of the first or second aspects of the invention, as shown in FIG. 15, an elastomeric material 143 may be disposed on the edges of the urease pouch 142. When the urease pouch 142 is placed in the sorbent cartridge 141, the elastomeric material 143 functions like the o-ring described above to create a seal and keep liquid from flowing around the urease pouch 142. The elastomeric material 143 can be made to completely cover the outside edges of the urease pouch 141, or the elastomeric material can be disposed in one or more thin strips of material. Alternatively, in any embodiment of the first or second aspects of the invention, the inside walls of the sorbent cartridge may be coated in an elastomeric substance, which will function to form the same seal when a rigid or semi-rigid urease pouch is placed within. In any embodiment of the first or second aspects of the invention, the urease pouches may be constructed to be slightly larger than the sorbent cartridge. When the user inserts the urease pouches into the sorbent cartridge, the urease pouch can be compressed slightly to fit in the sorbent cartridge. This will ensure that the urease pouches cover the entire area inside the sorbent cartridge and facilitate the forming of a seal around the edges of the urease pouch.

Figure 16:
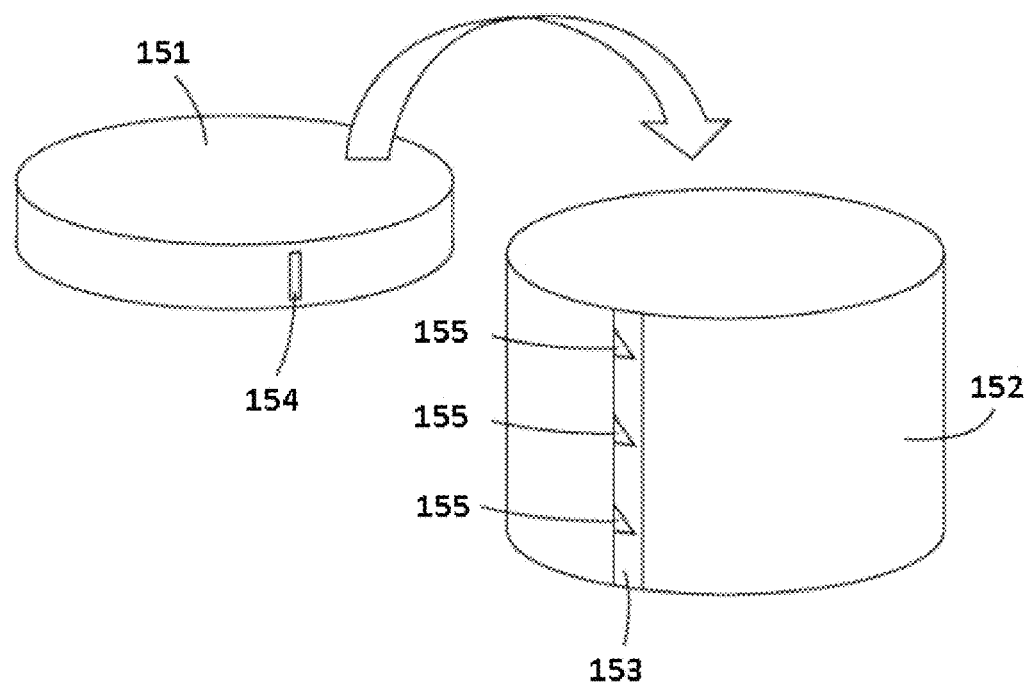
FIG. 16 is a perspective view of a urease pouch and cartridge with a key function to ensure correct alignment.

In any embodiment of the first or second aspects of the invention, ensuring that the urease pouches are properly inserted into the sorbent cartridge may be important. Any method of doing so is contemplated by this invention. One non-limiting example is shown in FIG. 16. Groove 153 may be created in the wall of the sorbent cartridge 152. A key 154, or flange, may be disposed on the side of the urease pouch 151. In order for the urease pouch 151 with key 154 to fit within the sorbent cartridge, the key 154 must be aligned with groove 153 in the sorbent cartridge wall. This will ensure that the urease pouch 151 is disposed within the sorbent cartridge 152 with the correct alignment. In any embodiment of the first or second aspects of the invention, optional ridges 155 may be placed within groove 153. The ridges 155 can serve to lock the urease pouch 151 in place vertically within the sorbent cartridge 152. The ridges 155 may be designed so that they are angled on the top portion of the ridge and flat on the bottom portion of the ridge. Once the key 154 passes a ridge 155 in a downward direction, the ridge 155 can serve to keep the urease pouch 151 from inadvertently moving back upward within the sorbent cartridge.

The ridges 155 may be designed such that the urease pouch 151 may be removed upward from the sorbent cartridge 152 only with the use of force greater than would be expected from inadvertent moving but not so much force as to prevent intentionally lifting the urease pouch out of the sorbent cartridge 152. This can be accomplished by using a semi-rigid material as either the key 154, the ridges 155, or both, such that when enough force is applied the key 154 or ridges 155 can be bent far enough to allow removal of the urease pouch 151 and then return to their original shape. Alternatively, the ridges 155 may be attached with a spring mechanism that is connected to a button (not shown), such that when the button is depressed the ridges 155 recede into the interior wall of the sorbent cartridge 152 and allow easy removal of the urease pouch 151 from the sorbent cartridge 152.

In any embodiment of the first or second aspects of the invention, the urease pouches may be loosely contained within the sorbent cartridge. The urease pouch need not be made the same size as, or larger than, the sorbent cartridge. One or more urease pouches may be constructed of a smaller size than the sorbent cartridge, and simply placed in the sorbent cartridge.

After construction of the urease pouch containing a sorbent material or materials, the material within the urease pouch can be washed so as to remove any particles smaller than the pore or mesh size of the urease pouch material. This will ensure that all particles within the urease pouch are large enough so that they cannot inadvertently pass out of the urease pouch. Thus, when used in a sorbent cartridge, the urease pouches themselves can act as a particulate filter, ensuring that no particulate matter of the sorbent material, or any other particulate matter, can pass downstream. This may eliminate the need for the use of external particulate filters.

In any embodiment of the first or second aspects of the invention, antimicrobial or antibacterial material may be impregnated into the urease pouch. This allows sterilization of the dialysate as the dialysate flows through the sorbent cartridge, and can eliminate the need for antimicrobial filters. In any embodiment of the first or second aspects of the invention, medication such as heparin or other anticoagulants, or antibiotics may be impregnated into the urease pouch. This can allow administration of these medications to the patient without the need for adding the drugs to the dialysate.

Figure 17:
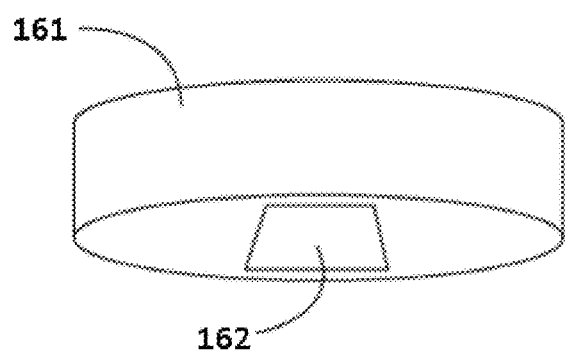
FIG. 17 is a perspective view of a urease pouch with a double layer of fabric in the center to control flow through the urease pouch.

In any embodiment of the first or second aspects of the invention, flow throughout the urease pouch can be controlled by variations in the urease pouch material. Generally, fluid moving through a conduit will move most quickly through the center of the conduit, and more slowly towards the edges. To ensure that fluid travels more evenly throughout the urease pouch, the urease pouch can be constructed such that more fluid enters the urease pouch on the outer edges of the urease pouch than enters in the center. One non-limiting example is shown in FIG. 17. A urease pouch 161, such as one made out of a fabric, can be constructed with an extra layer of fabric 162 in the center of the bottom portion of the urease pouch 161. This extra layer of fabric 162 effectively reduces the mesh size of the urease pouch in that location. With a smaller mesh size, resistance to flow will be greater in the center of the urease pouch 162, and fluid flow will be more evenly distributed to the edges of the urease pouch 162. In embodiments of the first or second aspects of the invention where the urease pouch is made out of metal or a polymer, the same effect can be created by making a smaller pore size, or alternatively less pores, in the center of the urease pouch. In any embodiment of the first or second aspects of the invention, a separator, similar to the one shown in FIG. 13, can be utilized in the middle of the urease pouch. The separator can be constructed as described above, such as with an extra layer of fabric near the center, to better control the flow of fluid throughout the urease pouch. Although shown in FIG. 17 as a centrally positioned rectangular layer, the extra layer of fabric 162 or other material may be positioned anywhere along the outer surface of the urease pouch 161, and may take any shape, such as circular, rectangular, triangular, etc. such that flow dynamics are altered.

In any embodiment of the first or second aspects of the invention, a patterned flow of fluid through the sorbent cartridge can be created. Occlusions, or blockages, of some of the pores can result in restricted flow through some portions of the urease pouch. In any embodiment of the first or second aspects of the invention, some of the pores in the urease pouch may be larger or smaller than other pores in the rest of the urease pouch. Flow will be increased through the larger pores as compared to the smaller pores, allowing control over fluid flow into and out of the urease pouch.

Figure 18A:
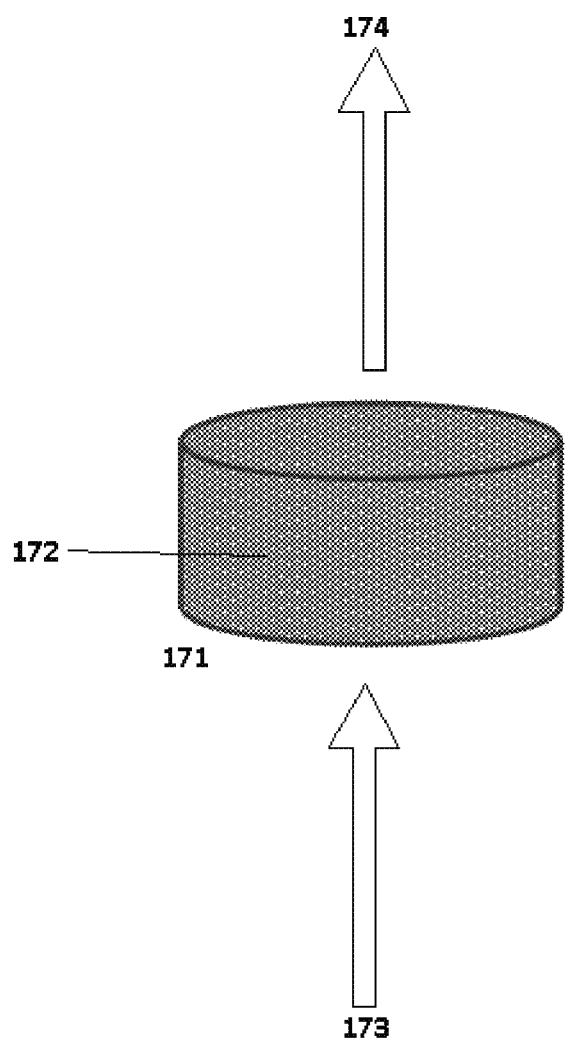
FIG. 18a is a perspective view of a urease pouch with a top and bottom surface that is permeable to dissolved urease.

In any embodiment of the first or second aspects of the invention, the mesh size of the urease pouches can be selected based on the need to keep urease within the pouch. In any embodiment of the first or second aspects of the invention, water and small dissolved molecules can pass through the urease pouch. For example, as shown in FIG. 18a, the mesh size of the urease pouch 171 can be such that urease 172 can pass through the urease pouch material through both the top and the bottom of the urease pouch 171, as shown by arrows 173 and 174. A urease pouch 172 can be used in embodiments of the first and second aspects of the invention where an alumina layer or silica layer is provided downstream of the urease pouch 171, as described herein. The user can place the urease pouch 172 into the sorbent cartridge. Once dissolved, the urease 172 can pass out of the urease pouch 171. The urease 172 can be immobilized by adsorption onto the alumina in the sorbent cartridge, where the urease can be used for dialysis. Because the bottom of the urease pouch is permeable to dissolved urease, the user can inject fresh urease into the sorbent cartridge, as explained herein, and the fresh urease can still be immobilized by the alumina downstream of the urease pouch 171. This is because the urease injected can travel through the urease pouch 171 and reach the downstream alumina layer. In any embodiment of the first or second aspects of the invention, alumina can be placed within the urease pouch 171 to immobilize urease within the urease pouch. A downstream alumina layer can still be provided to reduce urease migration.

Figure 18B:
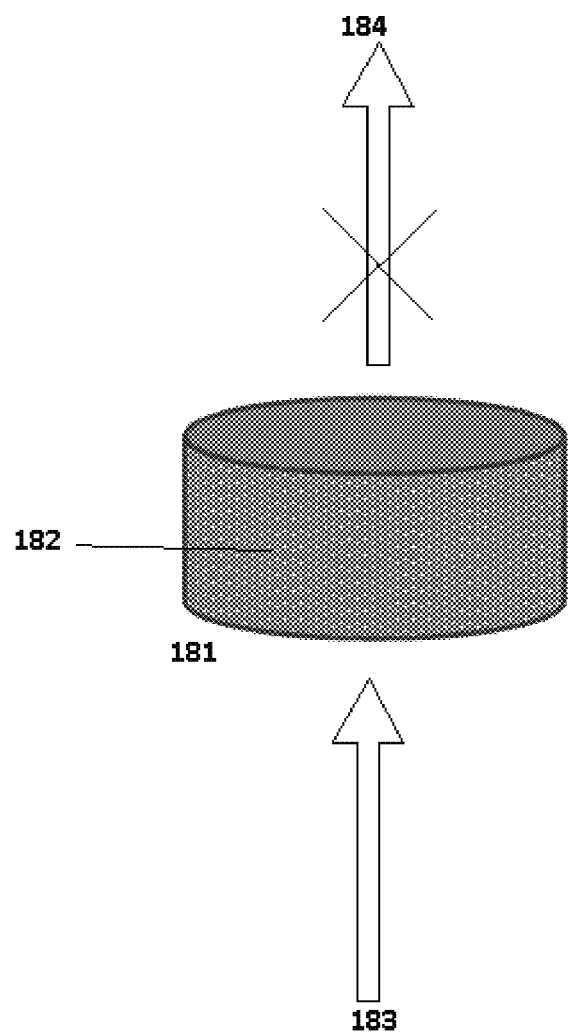
FIG. 18b is a perspective view of a urease pouch with a top surface that is impermeable to dissolved urease and a bottom section that is permeable to dissolved urease.

In any embodiment of the first or second aspects of the invention, as shown in FIG. 18b, the top of the urease pouch 181 can be made with a mesh size that does not allow dissolved urease to pass through the urease pouch 181, as shown by arrow 184, while the bottom of the urease pouch 181 can be made with a mesh size that does allow dissolved urease to pass into the urease pouch 181, as shown by arrow 183. In embodiments of the first and second aspects of the invention, such as the one shown in FIG. 18b, the urease 182 can enter the urease pouch 181 through the bottom of the urease pouch 181, but cannot exit through the top of the urease pouch 181. In order to replenish the urease in the sorbent cartridge, a new urease pouch 181 can be added to the system. Alumina is not necessary, because the urease 182 is immobilized, and unable to exit through the top of the urease pouch 181. In any embodiment of the first or second aspects of the invention using a urease pouch 181 as shown in FIG. 18b, a layer of alumina can still be provided in the urease pouch 181 or downstream of the urease pouch 181 in order to reduce urease migration. Urease introduced through an injection port as described herein can be used to replenish the urease when using a urease pouch 181. The urease solution that is injected can enter the urease pouch 181 through the bottom of the urease pouch 181, where the urease will be immobilized because the urease cannot exit the urease pouch 181.

Figure 18C:
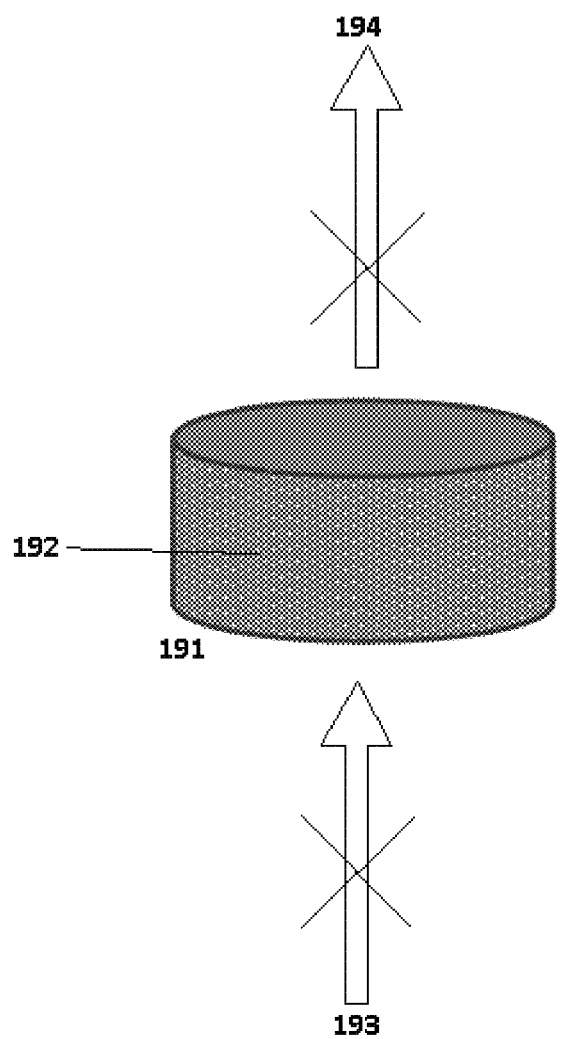
FIG. 18c is a perspective view of a urease pouch with top and bottom surfaces that are impermeable to dissolved urease.

In any embodiment of the first or second aspects of the invention, as shown in FIG. 18c, both the top layer and the bottom layer of the urease pouch 191 can be made with a mesh size small enough not to allow urease to pass through the urease pouch 191, as shown by arrows 193 and 194. Water and small molecules, such as urea, can still pass through the urease pouch 191 to react with the urease 192 within the urease pouch 191. In embodiments of the first or second aspects of the invention using a urease pouch 191 as shown in FIG. 18c, the urease 192 will be substantially retained within the urease pouch 191. Because the urease 192 cannot exit through the urease pouch 191, alumina may not be necessary for immobilization of the urease 192. However, a separate alumina layer can, in any embodiment of the first or second aspects of the invention, be used in order to prevent urease migration. In order to replenish the urease within the sorbent cartridge, a new urease pouch 192 can be added as explained herein.

One skilled in the art will understand that various combinations and/or modifications and variations can be made in the dialysis system depending upon the specific needs for operation. Moreover features illustrated or described as being part of an aspect of the invention may be included in the aspect of the invention, either alone or in combination.

We claim:

1. A sorbent cartridge, comprising:
a first section having a urease introducer configured to receive urease via one or more urease pouches containing solid urease constructed from a material that can allow fluid to freely pass through the urease pouch while substantially retaining solid urease in the urease pouch; wherein at least one urease pouch is positioned in the first section.

2. The sorbent cartridge of claim 1, further comprising a second section configured to contain one or more sorbent materials; and a fluid connection fluidly connecting the first section to the second section.

3. The sorbent cartridge of claim 2, wherein the first section further comprises at least one additional sorbent material selected from the group consisting essentially of activated carbon, zirconium oxide, alumina, silica, and combinations thereof, and wherein the one or more sorbent materials in the second section is selected from any one of zirconium phosphate, zirconium oxide, activated carbon, alumina, silica, and combinations thereof.

4. The sorbent cartridge of claim 3, wherein the one or more sorbent materials in either the first or second section is rechargeable.

5. The sorbent cartridge of claim 1, wherein the urease introducer is selected from any one of: a urease tray slideably disposed on the first section; and a urease door disposed on an exterior side of the sorbent cartridge allowing access into an interior of the first section.

6. The sorbent cartridge of claim 5, wherein the urease tray and interior of the first section are adapted to receive either a urease pouch containing urease or solid urease.

7. The sorbent cartridge of claim 6, wherein the urease pouch or solid urease contains alumina, silica, or a combination thereof.

8. The sorbent cartridge of claim 5 further comprising a valve disposed on the urease injection port for controlling an introduction of a urease solution into the first section.

9. The sorbent cartridge of claim 1, wherein the urease pouch has a planar base with upwardly extending walls connecting to a planar top wherein the walls are constructed from a rigid, fluid impermeable material.

10. The sorbent cartridge of claim 9, wherein the urease pouch has a base and top that are circular and wherein the upwardly extending walls (a) extend parallel to a flow path, (b) slope inward to an axis of the sorbent cartridge wherein the top has a smaller surface area than the base, or (c) upwardly slope outward from the axis of the disc shape wherein the top has a larger surface area than the base.

11. The sorbent cartridge of claim 1, wherein the urease pouch has any one of (i) a top of the urease pouch having a pore size small enough to prevent urease from passing through and a bottom portion of the urease pouch having a pore size to allow urease to pass through; (ii) a top of the urease pouch having a pore size to allow urease to pass through and a bottom portion of the urease pouch having a pore size small enough to prevent urease from passing through; or (iii) a top of the urease pouch having a pore size to allow urease to pass through and a bottom portion of the urease pouch having a pore size to allow urease to pass through.

12. The sorbent cartridge of claim 1, wherein the urease pouch has a shape selected from the group consisting of a circular shape, a square shape, a triangular shape, a rectangular shape, a disc shape, a cylindrical shape, a spherical shape, a substantially rectangular shape, and a cubical shape.

13. The sorbent cartridge of claim 1, further comprising a urea sensor disposed in a fluid flow path such that the urea sensor contacts fluid exiting the first section, and further comprising an alert that is triggered if the urea sensor detects urea in fluid exiting the first section.

14. The sorbent cartridge of claim 1, wherein the urease introducer is configured to receive an adjustable amount of urease.

15. The sorbent cartridge of claim 1, wherein the urease introducer is configured to receive a fixed or adjustable amount of urease.

16. The sorbent cartridge of claim 1, wherein the one or more sorbent pouches are removable and insertable.

* * * * *